United States Patent
Shi et al.

(10) Patent No.: US 11,103,725 B2
(45) Date of Patent: Aug. 31, 2021

(54) WIRELESS OPTOGENETIC DEVICE AND ASSOCIATED RADIATION SYSTEM

(71) Applicant: City University of Hong Kong, Kowloon (HK)

(72) Inventors: Peng Shi, Kowloon (HK); Ming Liu, Kowloon (HK); Xudong Lin, Kowloon (HK)

(73) Assignee: City University of Hong Kong, Kowloon (HK)

(*) Notice: Subject to any disclaimer, the term of this patent is extended or adjusted under 35 U.S.C. 154(b) by 44 days.

(21) Appl. No.: 15/695,372

(22) Filed: Sep. 5, 2017

(65) Prior Publication Data

US 2019/0070430 A1   Mar. 7, 2019

(51) Int. Cl.
| | | |
|---|---|---|
| *A61N 5/06* | (2006.01) | |
| *A61N 5/01* | (2006.01) | |
| *A61D 3/00* | (2006.01) | |
| *C09K 11/77* | (2006.01) | |
| *G06T 7/70* | (2017.01) | |
| *A61B 17/00* | (2006.01) | |
| *A61B 18/22* | (2006.01) | |

(Continued)

(52) U.S. Cl.
CPC ............. *A61N 5/0622* (2013.01); *A61D 3/00* (2013.01); *A61N 5/01* (2013.01); *A61N 5/0601* (2013.01);
(Continued)

(58) Field of Classification Search
CPC .......... A61D 3/00; A61N 5/01; A61N 5/0601; A61N 5/0618; A61N 5/0622; C09K 11/7705
See application file for complete search history.

(56) References Cited

U.S. PATENT DOCUMENTS

| | | | |
|---|---|---|---|
| 8,956,396 B1* | 2/2015 | Friend ................. | A61N 5/0622 607/88 |
| 2014/0148880 A1 | 5/2014 | Deisseroth et al. | |

(Continued)

OTHER PUBLICATIONS

Park Si, Brenner DS, Shin G, Morgan CD, Copits BA, Chung HU, et al. Soft, stretchable, fully implantable miniatmized optoelectronic systems for wireless optogenetics. Nat Biotechnol. 2015 ;33 : 1280-6.

(Continued)

*Primary Examiner* — Ankit D Tejani
(74) *Attorney, Agent, or Firm* — Renner Kenner Greive Bobak Taylor & Weber

(57) ABSTRACT

A wireless optogenetic device in proximity to a neural cell of a subject includes a body configured to hold light transducing materials arranged to up-convert electromagnetic radiation in infrared or near-infrared spectrum into light in the visible spectrum to affect activity of the neural cell. The body allows electromagnetic radiation in infrared or near-infrared to reach the light transducing materials. A radiation system includes a radiation probe for irradiating a wireless optogenetic device with electromagnetic radiation in infrared or near-infrared spectrum from a radiation source. The system further includes a movement mechanism for moving the radiation probe, a detector for detecting a location of the wireless optogenetic device, and a controller for controlling the movement mechanism based on the detected location of the wireless optogenetic device such that the radiation probe is arranged to irradiate the wireless optogenetic device at the detected location with the electromagnetic radiation.

33 Claims, 11 Drawing Sheets
(11 of 11 Drawing Sheet(s) Filed in Color)

(51) Int. Cl.
*A61N 5/067* (2006.01)
*G06T 7/20* (2017.01)

(52) U.S. Cl.
CPC ........ *A61N 5/0618* (2013.01); *C09K 11/7705* (2013.01); *A61B 2017/00057* (2013.01); *A61B 2017/00075* (2013.01); *A61B 2018/2272* (2013.01); *A61N 2005/063* (2013.01); *A61N 2005/067* (2013.01); *A61N 2005/0612* (2013.01); *A61N 2005/0626* (2013.01); *A61N 2005/0651* (2013.01); *A61N 2005/0659* (2013.01); *A61N 2005/0662* (2013.01); *A61N 2005/0665* (2013.01); *A61N 2005/0667* (2013.01); *G06T 7/20* (2013.01); *G06T 7/70* (2017.01)

(56) References Cited

U.S. PATENT DOCUMENTS

| | | | |
|---|---|---|---|
| 2015/0297719 A1* | 10/2015 | Deisseroth | A61P 25/24 604/20 |
| 2016/0066789 A1* | 3/2016 | Rogers | A61N 1/05 604/20 |
| 2016/0157706 A1 | 6/2016 | Pisanello et al. | |
| 2016/0317658 A1 | 11/2016 | Deisseroth et al. | |
| 2019/0090801 A1* | 3/2019 | Rogers | A61B 5/4064 |

OTHER PUBLICATIONS

Wu X, Zhang Y, et al. Dye-Sensitized Core/Active Shell Upconversion Nanoparticles for Optogenetics and Bioimaging Applications. Acs Nano. 2016;10:1060-6.

Shoko Hososhima et al; Near-infrared (NIR) up-conversion optogenetics; Scientific Reports | 5:16533 | DOI: 10.1038/srep16533.

Kate L Montgomery et al; Wirelessly powered, fully internal optogenetics for brain, spinal and peripheral circuits in mice; Nat Methods. 2015; 12:969-74.

Christian T. Wentz et al; A Wirelessly Powered and Controlled Device for Optical Neural Control of Freely-Behaving Animals; J Neural Eng. Aug. 2011 ; 8(4): 046021. doi:10.1088/1741-2560/8/4/046021.

* cited by examiner

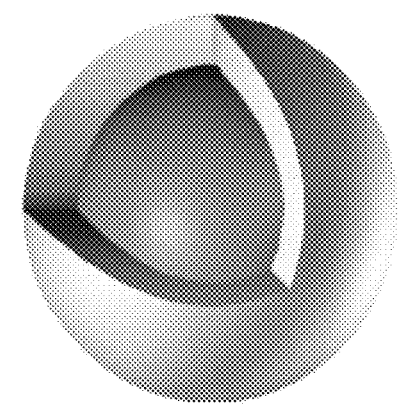
Figure 2A
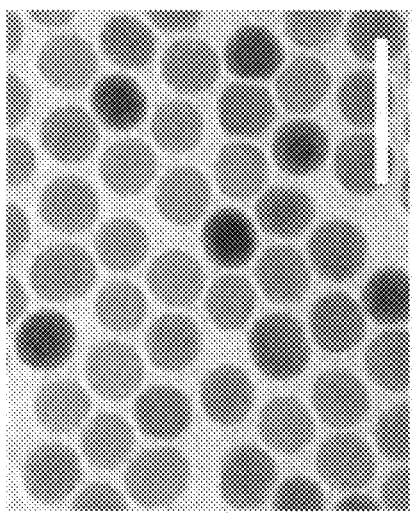
Figure 2B
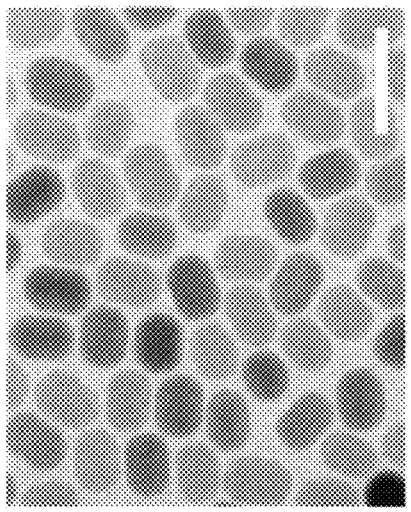
Figure 2C
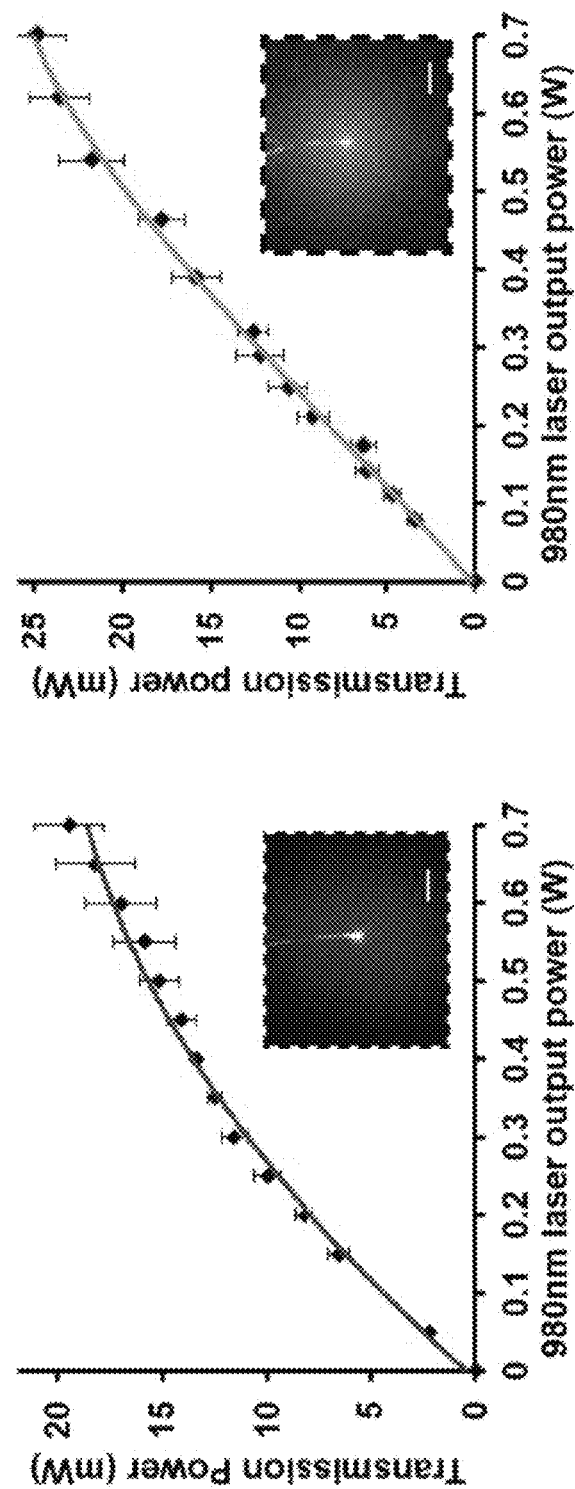
Figure 2D
Figure 2E

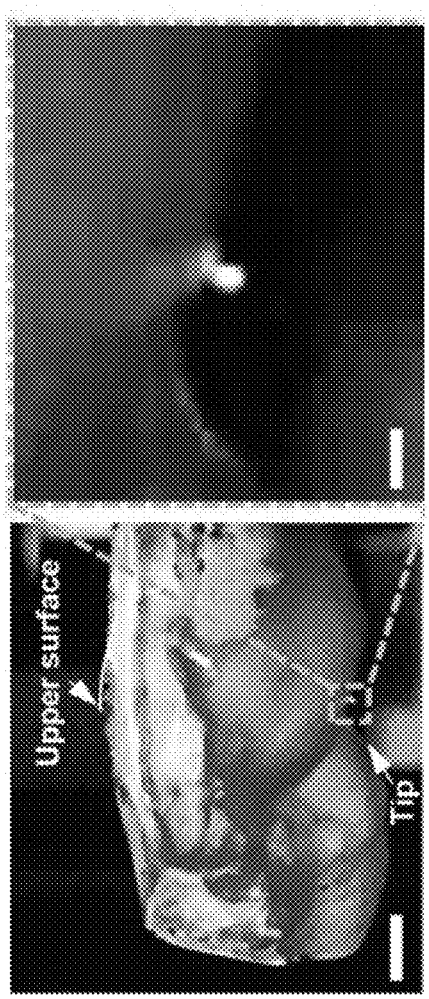
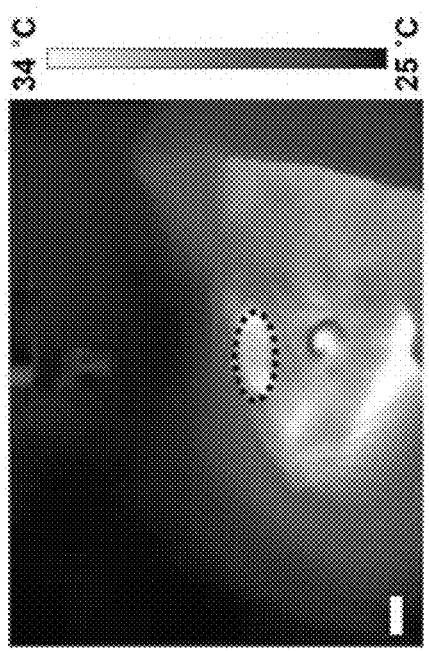
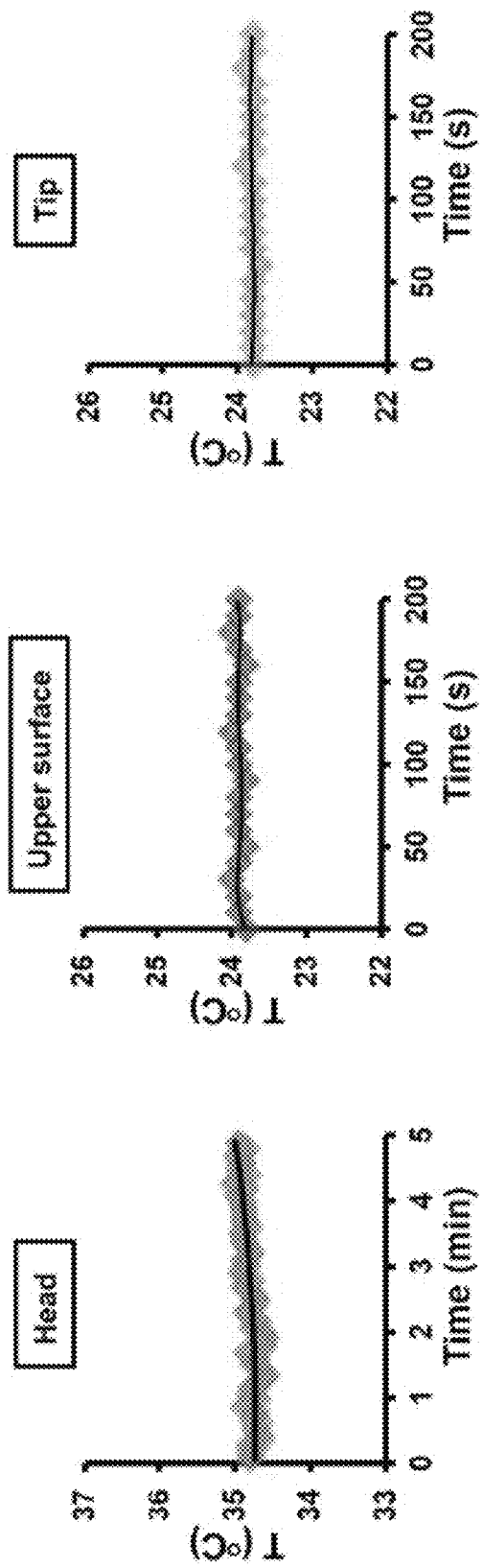
Figure 3B
Figure 3A
Figure 3E
Figure 3D
Figure 3C

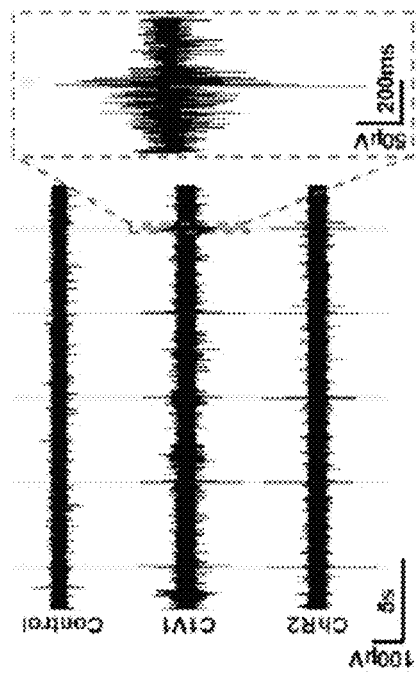
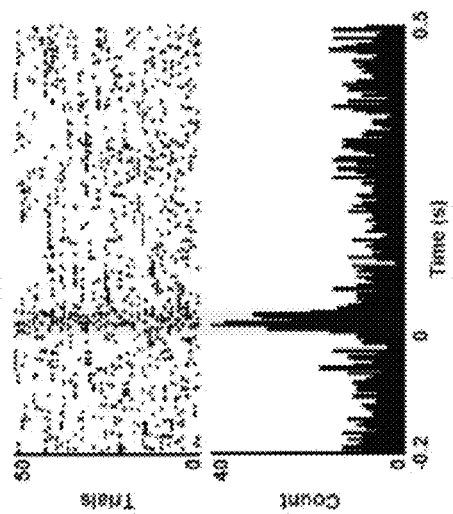
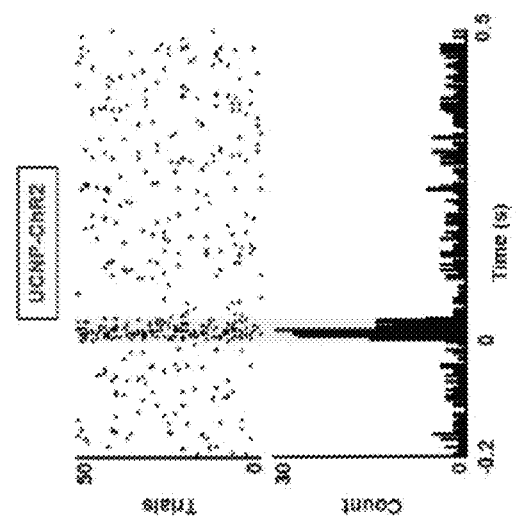
Figure 4A
Figure 4B
Figure 4C
Figure 4D

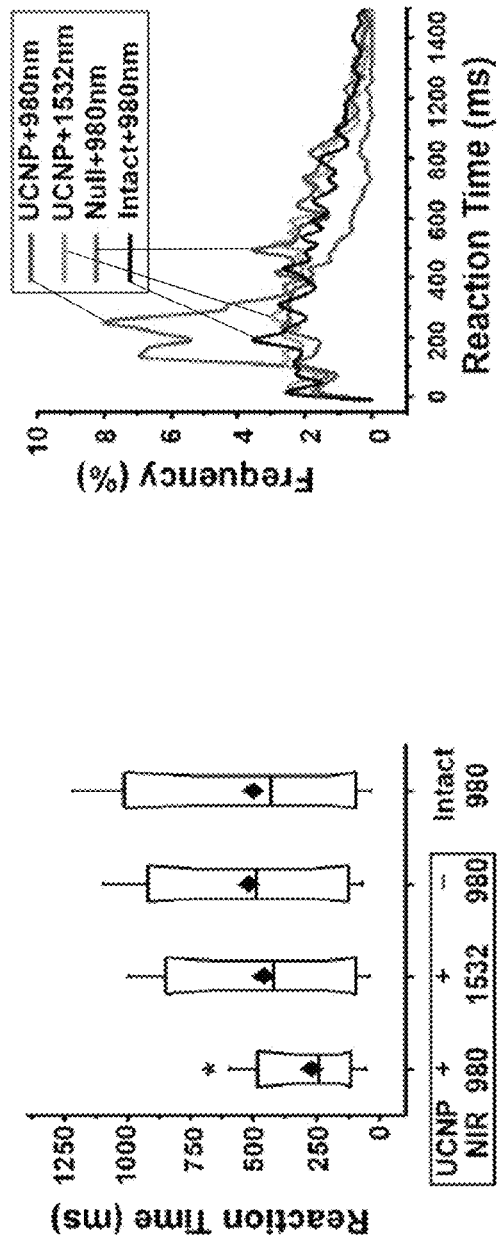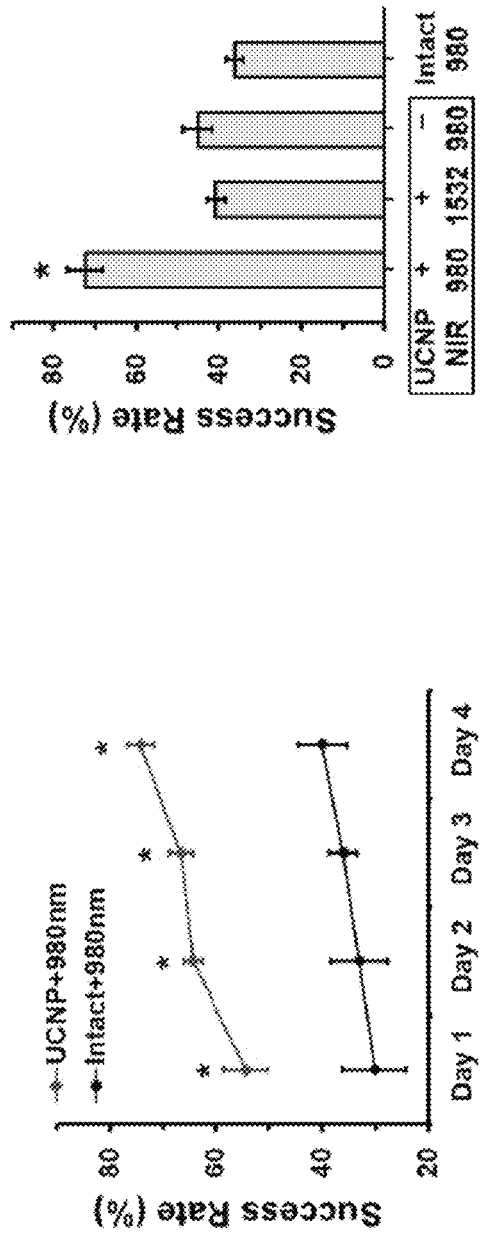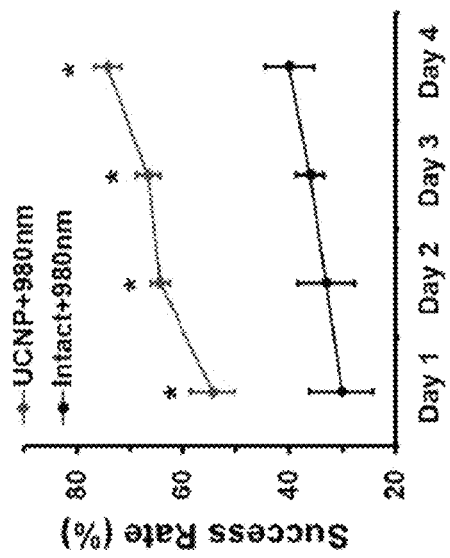

WIRELESS OPTOGENETIC DEVICE AND ASSOCIATED RADIATION SYSTEM

TECHNICAL FIELD

The invention relates to a wireless optogenetic device and an associated radiation system for realizing optical-based wireless remote control of neural activities in subjects such as non-human animals.

BACKGROUND

Electrical, optical, and chemical manipulations of neural circuits have been major approaches used to elucidate the functions and connections of the nervous system. Recently, optogenetics has become a versatile and transformative tool for neuroscience studies. The technique is based on optical stimulation of light-sensitive ion channels genetically expressed on cell membranes, and thus allows for spatially and temporally precise control over neural activity. Since the first demonstration using channelrhodopsin-2 (ChR2), various photosensitive proteins have been developed to provide flexible options for optogenetic applications. Most of these proteins are activated by light within the visible spectrum (VIS), which has limited tissue penetration and can lead to great photo-toxicity following prolonged exposure. Existing optogenetic experiments usually require light delivery by implanted optic fibers connected to a light source. In many behavioral tests, such systems prevent animals from moving freely, impose significant constraints on experimental design, and complicate the analysis of animal behavior.

SUMMARY OF THE INVENTION

In accordance with a first aspect of the invention, there is provided a wireless (tether-less) optogenetic device arranged to be placed in proximity to a neural cell of a subject, comprising: a body configured to hold light transducing materials (of sufficient concentration) which, when exposed to an electromagnetic radiation in infrared or near-infrared spectrum, are arranged to up-convert the electromagnetic radiation into light in visible spectrum to affect activity of (e.g., stimulate and inhibit) the neural cell; wherein the body is configured to allow electromagnetic radiation in infrared or near-infrared spectrum from a remote radiation system to reach the light transducing materials therein to perform up-conversion. Preferably, the light transducing materials are arranged in the body. The wireless optogenetic device removes the need of an implanted light source, allows movement of the subject during up-conversion, reducing constrains on the subject, and minimizing effect on the subject's behavior.

In a preferred embodiment of the first aspect, the wireless optogenetic device is free of electrical components. Complexity of the device can thus be substantially reduced.

In one embodiment of the first aspect, the body is tapered towards a tip and the light transducing materials are at least arranged at the tip. This enables concentrated light emission at the tip. In one embodiment of the first aspect, the body has a circular cross-section with a maximum diameter of 100 µm. In one embodiment of the first aspect, weight of the wireless optogenetic device is less than 1 mg. This specific dimension and weight reduce the damage to the tissue of the subject when the wireless optogenetic device is placed (e.g., implanted) near the neural cell. They also permit multiple wireless optogenetic devices to be used on the same subject simultaneously.

In one embodiment of the first aspect, the body is biocompatible. Toxic effect can thus be minimized.

In one embodiment of the first aspect, the body is made of at least one of: glass, polydimethylsiloxane, and gel. In one example, the body is made of borosilicate glass.

In one embodiment of the first aspect, the body is substantially transparent. This reduces interference to the electromagnetic radiation provided from the remote radiation system, which in turn increases penetration of the electromagnetic radiation.

In one embodiment of the first aspect, the body is coated with a light reflecting layer having one or more optical windows at which the at least some light transducing materials are arranged. This allows up-converted light to be emitted only at specific locations corresponding to the optical windows for selective neural activity control.

In one embodiment of the first aspect, the body has a plurality of optical windows, and at least two different types of light transducing materials are arranged at two different optical windows of the plurality of optical windows. This allows different types of up-converted light to be emitted at different locations corresponding to the optical windows for more complex neural activity control.

In one embodiment of the first aspect, the body is sealed to enclose the light transducing materials. Direct contact between light transducing materials and the neural cell of the subject is prevented, and safety is improved.

In one embodiment of the first aspect, the light transducing materials in the body are dry. In general dry light transducing materials last longer. In another embodiment of the first aspect, the light transducing materials in the body are wet.

In one embodiment of the first aspect, the light transducing materials comprises nanomaterials. The nanomaterials may be lanthanide-doped nanoparticles. The lanthanide metal is selected from the group consisting of Lanthanum, Cerium, Praseodymium, Neodymium, Promethium, Samarium, Europium, Gadolinium, Terbium, Dysprosium, Holmium, Erbium, Thulium, Ytterbium, and Lutetium. The nanomaterials may be NaYF4-based nanoparticles. Optionally, the nanomaterials may comprise at least one of: NaYF4:Yb/X@NaYF4 core-shell (NaYF4:Yb/X core and NaYF4 shell) nanocrystals and NaYF4@NaYF4:Yb/X@NaYF4 core-shell-shell (NaYF4 core, NaYF4:Yb/X shell, and NaYF4 shell) nanocrystals, where X is Erbium (Er), Thulium (Tm), or Er/Tm. Additionally or alternatively, the nanoparticles may comprise Na YF4:Ytterbium/X/Gadolinium, where X is Erbium (Er), Thulium (Tm), or Er/Tm.

In one embodiment of the first aspect, the electromagnetic radiation is upconverted into visible light having a wavelength corresponding to red, yellow, amber, green, or blue light.

In a preferred embodiment of the first aspect, the electromagnetic radiation has a wavelength of 700 nm to 1100 nm. Such wavelength allows deep tissue penetration, has relatively low absorbance by biomolecules, and would produce minimal photo-induced damage to the cells.

In a preferred embodiment of the first aspect, the electromagnetic radiation in infrared or near-infrared spectrum is in the form of laser.

In one embodiment of the first aspect, the neural cell comprises neurons expressing opsin proteins.

In one embodiment of the first aspect, the neural cell is a neural cell in a central nervous system or a peripheral nervous system of the subject.

In one embodiment of the first aspect, the subject is a non-human animal. In another embodiment of the first aspect, the subject is a human.

In accordance with a second aspect of the invention, there is provided a radiation system arranged to remotely irradiate a wireless optogenetic device placed in proximity to a neural cell of a subject; the wireless optogenetic device comprising a body holding light transducing materials which, when exposed to an electromagnetic radiation in infrared or near-infrared spectrum, are arranged to up-convert the electromagnetic radiation into light in visible spectrum to affect activity of the neural cell, and the body is configured to allow electromagnetic radiation in infrared or near-infrared spectrum from a remote radiation system to reach the light transducing materials therein to perform up-conversion; the radiation system comprising: a radiation probe arranged to be connected with a radiation source, for irradiating a wireless optogenetic device with electromagnetic radiation in infrared or near-infrared spectrum; a movement mechanism operably connected with the radiation probe for moving the radiation probe; a detector for detecting a location of the wireless optogenetic device; and a controller for controlling the movement mechanism to affect movement of the radiation probe based on the detected location of the wireless optogenetic device such that the radiation probe is arranged to irradiate the wireless optogenetic device at the detected location with the electromagnetic radiation. The radiation system allows remote radiation to be supplied to the optogenetic device such that the optogenetic device does not require a local radiation source or any wires or tethers associated with such radiation source.

In one embodiment of the second aspect, the radiation system further comprises the radiation source.

In one embodiment of the second aspect, the radiation probe is arranged to provide electromagnetic radiation with a wavelength of 700 nm to 1100 nm. Such wavelength allows deep tissue penetration, has relatively low absorbance by biomolecules, and would produce minimal photo-induced damage to the cells.

In one embodiment of the second aspect, the radiation system further comprises a bounded platform defining an area in which the subject can move. The bounded platform may comprise a physical boundary (e.g., walls) or a virtual boundary (e.g., a wired boundary"). This enables the subject to be confined in a space in which the radiation system is best adapted for operation.

In one embodiment of the second aspect, the movement mechanism is arranged to rotate or translate the radiation probe. In other words, the movement mechanism may both rotate and translate the radiation probe. Targeted radiation can thus be provided.

In one embodiment of the second aspect, the movement mechanism comprises a motorised arm to which the radiation probe is mounted.

In one embodiment of the second aspect, the radiation source comprises continuous wave laser diode. Such diode is relatively cheap and is readily available.

In one embodiment of the second aspect, the radiation probe comprises a collimator for directing electromagnetic radiation emitted by the continuous wave laser diode. Electromagnetic radiation can be better focused, confined, and directed to a target point with higher resolution.

In one embodiment of the second aspect, the detector is arranged for tracking real time movement of the subject; and the controller is arranged to control the movement mechanism to affect movement of the radiation probe to continuously irradiate the wireless optogenetic device with the electromagnetic radiation during movement of the subject. Real time, automatic tracking of the subject so that reduced constrain or stress is placed on the subject.

In one embodiment of the second aspect, the radiation system further comprises an optical component arranged to alter one or more properties of the electromagnetic radiation provided by the radiation source, the one or more properties comprises: the wavelength of the electromagnetic radiation, the intensity of the electromagnetic radiation, the power of the electromagnetic radiation, the duration of a pulse of the electromagnetic radiation, the power of a pulse of the electromagnetic radiation, and the frequency of pulses of the electromagnetic radiation.

In one embodiment of the second aspect, the detector comprises a camera.

In one embodiment of the second aspect, the subject is a non-human animal. In another embodiment of the second aspect, the subject is human.

In accordance with a third aspect of the invention, there is provided a system for controlling activity of a neural cell of a subject, comprising: (1) a wireless optogenetic device arranged to be placed in proximity to a neural cell of a subject, comprising a body configured to hold light transducing materials which, when exposed to an electromagnetic radiation in infrared or near-infrared spectrum, are arranged to up-convert the electromagnetic radiation into light in visible spectrum to affect activity of the neural cell; and allow electromagnetic radiation in infrared or near-infrared spectrum from a remote radiation system to reach the light transducing materials therein to perform up-conversion; and (2) a radiation system arranged to remotely irradiate the wireless optogenetic device, comprising: a radiation probe arranged to be connected with a radiation source, for irradiating a wireless optogenetic device with electromagnetic radiation in infrared or near-infrared spectrum; a movement mechanism operably connected with the radiation probe for moving the radiation probe; a detector for detecting a location of the wireless optogenetic device; and a controller for controlling the movement mechanism to affect movement of the radiation probe based on the detected location of the wireless optogenetic device such that the radiation probe is arranged to irradiate the wireless optogenetic device at the detected location with the electromagnetic radiation.

In a preferred embodiment of the third aspect, the wireless optogenetic device is the wireless optogenetic device of the first aspect. In other words, features relating to the first aspect are also applicable to the third aspect.

In a preferred embodiment of the third aspect, the radiation system is the radiation system of the second aspect. In other words, features relating to the second aspect are also applicable to the third aspect.

In accordance with a fourth aspect of the invention, there is provided a method for controlling activity of a neural cell of a subject, comprising: placing a wireless optogenetic device in proximity to the neural cell of the subject, the wireless optogenetic device comprising a body holding light transducing materials which, when exposed to an electromagnetic radiation in infrared or near-infrared spectrum, are arranged to up-convert the electromagnetic radiation into light in visible spectrum to affect activity of the neural cell, and the body is configured to allow electromagnetic radiation in infrared or near-infrared spectrum from a remote radiation system to reach the light transducing materials therein to perform up-conversion; and remotely irradiating the wireless optogenetic device using a remote radiation system.

In a preferred embodiment of the fourth aspect, the wireless optogenetic device is the wireless optogenetic device of the first aspect. In other words, features relating to the first aspect are also applicable to the fourth aspect.

In a preferred embodiment of the fourth aspect, the radiation system is the radiation system of the second aspect. In other words, features relating to the second aspect are also applicable to the fourth aspect.

In one embodiment of the fourth aspect, the method further comprises: detecting, using the remote radiation system, a location of the wireless optogenetic device; and irradiating, using the remote radiation system, the wireless optogenetic device based on the detected location.

In one embodiment of the fourth aspect, the step of detecting a location of the wireless optogenetic device comprises tracking real time movement of the subject; and wherein the step of irradiating the wireless optogenetic device based on the detected location comprises continuously irradiating the wireless optogenetic device with the electromagnetic radiation during movement of the subject.

In one embodiment of the fourth aspect, the method is arranged for in vivo behavioral conditioning or behavioral control of the subject.

In one embodiment of the fourth aspect, the subject is a non-human animal. In another embodiment of the fourth aspect, the subject is a human.

In accordance with a fifth aspect of the invention, there is provided a method of manufacturing a wireless optogenetic device, comprising: (a) forming a receptacle with open ends, the receptacle being configured to hold light transducing materials which, when exposed to an electromagnetic radiation in infrared or near-infrared spectrum, are arranged to up-convert the electromagnetic radiation into light in visible spectrum to affect activity of the neural cell; and allow electromagnetic radiation in infrared or near-infrared spectrum from a remote radiation system to reach the light transducing materials to perform up-conversion; (b) placing the light transducing materials in the receptacle; and (c) sealing at least one end of the receptacle to form the wireless optogenetic device.

In a preferred embodiment of the fifth aspect, the wireless optogenetic device is the wireless optogenetic device of the first aspect. In other words, features relating to the first aspect are also applicable to the fifth aspect.

In one embodiment of the fifth aspect, the receptacle is substantially transparent.

In one embodiment of the fifth aspect, step (a) comprises: pulling a glass capillary tube to form a pulled pipette that defines the receptacle.

In one embodiment of the fifth aspect, step (b) comprises: placing light transducing materials dispersed in a solvent in the receptacle; and evaporating the solvent to dry the light transducing materials in the receptacle.

In one embodiment of the fifth aspect, the solvent comprises cyclohexane.

In one embodiment of the fifth aspect, step (c) comprises: heating one end of the receptacle for sealing.

In one embodiment of the fifth aspect, step (c) further comprises: sealing the other end of the receptacle with a sealant.

In one embodiment of the fifth aspect, the sealant comprises epoxy.

In one embodiment of the fifth aspect, the receptacle is formed to taper towards a tip.

Other advantages of the invention will become apparent by referring to the description with reference to the drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention will now be described, by way of example, with reference to the accompanying drawings in which:

FIG. 1A is a schematic diagram showing wireless near-infrared (NIR) optogenetic control of brain activity using an implantable wireless optogenetic device in one embodiment of the invention;

FIG. 1B are bright-field and fluorescent photographs of the implantable wireless optogenetic devices in one embodiment of the invention respectively containing up-conversion nanoparticles (UCNPs) doped with $Tm^{3+}$ (blue) and $Er^{3+}$ (green), scale bar=500 μm;

FIG. 1O are fluorescent images of the operating UCNP optogenetic devices ($Tm^{3+}$-doped, blue; $Er^{3+}$-doped, green) excited by NIR in one embodiment of the invention, scale bar=2 mm;

FIG. 1D are images of animals implanted with optogenetic devices in one embodiment of the invention containing $Tm^{3+}$-doped UCNPs (top) and $Er^{3+}$-doped (bottom) UCNPs, scale bar=1 cm;

FIG. 1E is a schematic diagram showing the design of a radiation projection system in one embodiment of the invention for automatic and consistent NIR irradiation of the heads of animals implanted with the optogenetic devices;

FIGS. 2A-2E illustrate physical characterization of the upconversion-based optogenetic device in one embodiment of the invention, and in particular:

FIG. 2A shows a schematic diagram of the core-shell structure of UCNPs used in one embodiment of the invention;

FIG. 2B shows transmission electron microscopy (TEM) images of UCNPs with a NaYF4:Yb/Er core used in one embodiment of the invention, scale bar=100 nm;

FIG. 2C shows transmission electron microscopy (TEM) images of UCNPs in the form of NaYF4:Yb/Er@NaYF4 core-shell nanoparticles used in one embodiment of the invention, scale bar=100 nm;

FIG. 2D is a graph showing the power of blue light emission from the optogenetic devices in one embodiment of the invention containing UCNPs doped with $Tm^{3+}$ at various powers of the 980 nm laser, scale bar=2 mm;

FIG. 2E is a graph showing the power of green light emission from the optogenetic devices in one embodiment of the invention containing UCNPs doped with $Er^{3+}$ at various powers of the 980 nm laser, scale bar=2 mm;

FIGS. 3A-3E illustrate thermal characterization of NIR irradiation used to actuate upconversion-based optogenetic device in one embodiment of the invention, and in particular:

FIG. 3A shows an image obtained by infrared imaging of a live rat's brain under pulsed NIR laser irradiation with the rat's head exposed to a pulsed 980 nm laser (50 ms width, 10 pulses, 10 Hz, 8 mW/mm$^2$) for 5 minutes, scale bar=5 mm, FIG. 3B show images for evaluating temperature fluctuation at the tip of a the optogenetic devices in one embodiment of the invention containing UCNPs after implantation through an isolated rat brain, scale bar=2.5 mm; also, the enlarged boxed region shows the green light emission from the tip of the optogenetic device remotely actuated by NIR irradiation above the skull, scale bar=500 μm; wherein the isolated rat's head was exposed to a pulsed 980 nm laser (50 ms width, 10 pulses, 10 Hz, 8 mW/mm$^2$) for over 200 seconds;

FIG. 3C is a graph showing temperature fluctuation at the center point of the NIR-irradiated region circled in FIG. 3A;

FIG. 3D is a graph showing temperature fluctuation at the upper surface of the rat's head in FIG. 3B;

FIG. 3E is a graph showing temperature fluctuation at the tip of the optogenetic device in FIG. 3B;

FIGS. 4A-4D illustrate in vivo neural stimulation using an implanted UCNP device in one embodiment of the invention, and in particular:

FIG. 4A is a schematic diagram showing upconversion-based neural stimulation and extracellular recording in brains of anesthetized animals in one embodiment of the invention;

FIG. 4B show representative recordings of NIR-driven spiking traces in animals expressing different ChR variants (ChR2 and C1V1), wherein radiation from a 980 nm laser was applied at 2 Hz (40 ms pulse width, 4.4 mW/mm$^2$ for C1V1 animals; and 7 mW/mm$^2$ for ChR2 animals), and the C1V1 animals were implanted with a null-optogenetic device of the invention (i.e., device without UCNPs) as control;

FIG. 4C is a raster plot and pen-stimulus time histogram (PSTHs, 5 ms/bin, 50 trials) showing the temporal correlation between increased spiking activity and NIR illumination in ChR2 animals (40 ms pulse width, 7 mW/mm$^2$) as tested in FIG. 4B;

FIG. 4D is a raster plot and pen-stimulus time histogram (PSTHs, 5 ms/bin, 50 trials) showing the temporal correlation between increased spiking activity and NIR illumination in C1V1 animals (40 ms pulse width, 4.4 mW/mm$^2$) as tested in FIG. 4B;

FIG. 5A is a picture showing a radiation projection system in one embodiment of the invention as part of the upconversion-based neural stimulation strategy, scale bar=2 cm; wherein the mouse's head is enlarged to show the emission of green light from the implanted UCNP-optogenetic device in one embodiment of the invention under NIR irradiation at 5 mW/mm$^2$, scale bar=5 mm;

FIG. 5B is a schematic diagram showing the experimental configuration of unilateral stimulation in the mouse cortical striatum using NIR irradiation;

FIG. 5C show representative pre-stimulation motion-paths from a C1V1 mouse;

FIG. 5D show representative motion-paths from the C1V1 mouse tested in FIG. 5C with its cortical striatum activated by the upconversion-based neural stimulation method in one embodiment of the invention;

FIG. 5E show representative post-stimulation motion-paths from the C1V1 mouse tested in FIG. 5C, FIG. 5F is a graph showing quantitative analysis of rotational movements (contraversive vs. ipsiversive) before (pre-stim.), during (NIR-stim.), and after (post-stim.) NIR illumination; in the tests for the analysis, mice were evaluated one month and six months after surgical implantation of the UCNP-optogenetic device, and subjects with and without C1V1 infection in the striatum were used as test and control groups, respectively; for the one-month experiment, data from 20 sessions were collected from 5 mice; for the six-month experiment, data from 10 sessions were collected from 4 mice; error bars indicate s.e.m. *$p<0.001$ by one way analysis of variance; in the tests, the NIR laser (20 Hz, 10 ms pulse width, 5 mW/mm$^2$) was consistently applied using a radiation projection system in one embodiment of the invention;

FIG. 6A is a schematic diagram showing a Y-maze used in the experiment in one embodiment of the invention;

FIG. 6B are pictures showing expression of C1V1 in tyrosine hydroxylase (TH)$^+$ dopamine neurons (indicated by arrowheads) in the ventral tegmental area of the mouse brain 3 weeks after injection of adeno-associated viruses; wherein the fluorescence images of the boxed regions are enlarged in the right panels for clarity, scale bars=200 μm (left images) and 20 μm (right, enlarged images);

FIG. 6C is a graph showing quantification of the percentage of total nose-pokes in the "Active" arm of a Y-maze over a one-hour period in the experiment, wherein each poke in the "Active" arm was paired with a pulsed 980 nm laser (500 ms, 20 Hz, 10 ms pulse width, 5 mW/mm$^2$) (n=5, error bars indicate s.e.m., *$p<0.01$ by one way analysis of variance ANOVA);

FIG. 6D is a graph showing quantification of the percentage of total nosepokes in an "Inactive" arm of the Y-maze over the one-hour period in the experiment (n=5, error bars indicate s.e.m., *$p<0.01$ by one way ANOVA);

FIG. 6E are heat maps showing mouse (C1V1 and Wild-type) activity frequency in the post-condition session, wherein red color represents more frequent appearance in specific parts of the Y-maze;

FIG. 6F is a graph showing quantification of the appearance probability pre- and post-NIR conditioning sessions (n=5, error bars indicate s.e.m., *$p<0.01$ by one way ANOVA), wherein higher probabilities demonstrate the development of location preference in C1V1 mice;

FIG. 6G is a temporal curve of the animals' preference indices during the different stages of the experiment, wherein a decrease in the index reflects an increase in the predictability of the animal's movement (n=5 mice, error bars indicate s.e.m., *$p<0.01$ by one way ANOVA);

FIG. 6H are fluorescence images of a horizontal section of mouse brain showing the activation of c-fos in TH$^+$ dopamine neurons (indicated by arrowheads) surrounding the UCNP-optogenetic device (outlined) after repeated NIR irradiation for 1 hour (5 mW/mm$^2$, 10 ms pulse width, 20 Hz, 10 pulses were applied at the beginning of every minute), scale bar=20 μm;

FIGS. 7A-7H illustrate implantation of multiple UCNP-optogenetic devices of the invention for modulation of reflexive learning in rats in one embodiment of the invention, and in particular:

FIG. 7A is a schematic diagram of surgical implantation of multiple UCNP-optogenetic devices in one embodiment of the invention;

FIG. 7B is a photograph of a rat after implantation, scale bar=1 cm;

FIG. 7C are schematic diagrams illustrating reaction time tasks using NIR-induced cortical activation as a cue, wherein trials were initiated upon pokes into the left port; after a random holding period, a 980 nm laser (10 pulses, 10 Hz, 50 ms width, 1.5 mW/mm$^2$) was used to stimulate the animal's visual cortex; this stimulation then cued the animal to move to the right port for a water reward;

FIG. 7D are X-Ray and fluorescence images (top row, lateral view; bottom row, dorsal view) showing the colocalization of micro-optogenetic devices implants of the invention and ChR2 expression regions, wherein the micro-optogenetic devices are indicated by red arrows in the X-Ray images, scale bar=1 cm;

FIG. 7E is a graph of box-plots showing the quantification of the animals' reaction times in response to NIR cues; the different parts of the box-plots indicate 10th, 25th, 50th, 75th, and 90th percentiles, while the whiskers indicate the 5th and 95th percentiles; the diamond indicates the mean of the data, wherein*$p<0.001$ by Kruskal-Wallis analysis; wherein the experimental conditions include the use of UCNP-optogenetic devices of the invention illuminated by 980 nm or 1532 nm lasers, null-optogenetic devices of the invention illuminated by a 980 nm laser, and intact animals illuminated by a 980 nm laser; and at least 1,000 trials were performed in 4 rats for each condition;

FIG. 7F is a histogram of reaction times for the experimental and control groups used in the test for FIG. 7E;

FIG. 7G is a graph showing success rates of animals used in the test for FIG. 7E performing the reaction-time tasks in the first 4 days (n=4, error bars indicate s.e.m., *$p<0.001$ by ANOVA); and FIG. 7H is a graph showing success rates of animals used in the test for FIG. 7E after training for 4 days (n=4, error bars indicate s.e.m., *$p<0.001$ by ANOVA).

DETAILED DESCRIPTION OF THE PREFERRED EMBODIMENT

System Design

The inventors of the invention have devised, through experiments and trials, that the emission of visible light from upconversion may result from sequential discrete absorption of two or more lower-energy photons. The inventors of the invention realized that although this process can potentially enable the implementation of a method using NIR to stimulate neurons expressing commonly used light sensitive ion channel proteins (e.g., ChR2 and C1V1), several technical challenges must be overcome before any practical implementation. First, the UCNPs need to be implanted in a biocompatible receptacle with sufficient concentration, so that the implants are not toxic and the upconversion emission is sufficient to evoke optogenetic response. Second, the NIR irradiation has to target a specific part of the body of the freely moving animal (e.g., head for brain stimulation) for consistent tetherless delivery of stimulus signals.

Figure 1A:
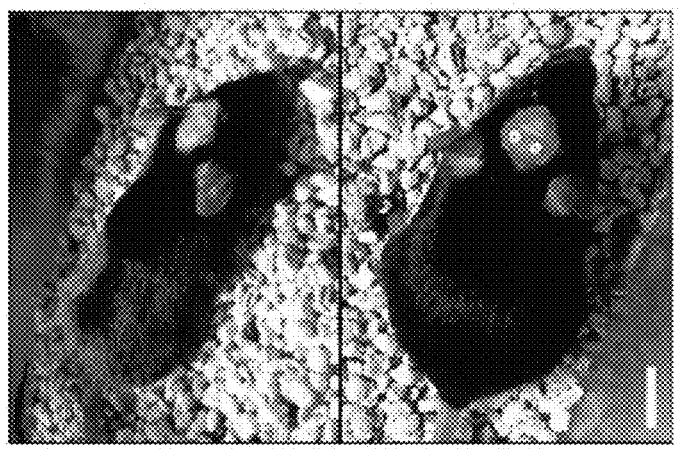
FIGS. 1A-1E illustrate upconversion-based neural stimulation technique in one embodiment of the invention, and in particular.
Figure 1B:
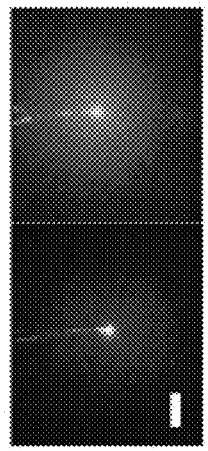
Figure 1C:
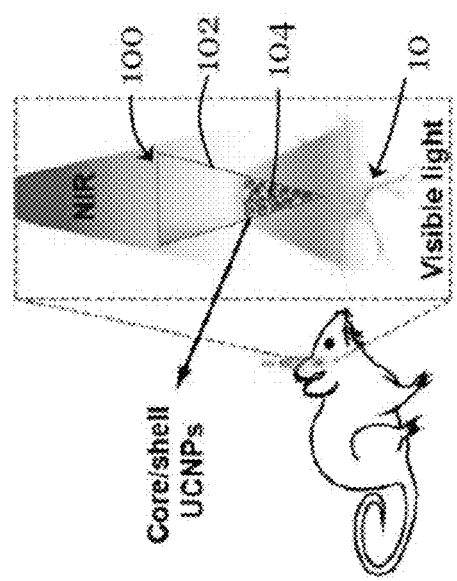

FIGS. 1A-1C show a fully implantable wireless optogenetic transducer device 100 in one embodiment of the invention. The wireless optogenetic device 100 is arranged to be placed in proximity to a neural cell 10 of a subject. The device 100 includes a body 102 configured to hold light transducing materials 104 which, when exposed to an electromagnetic radiation in infrared or near-infrared spectrum, are arranged to up-convert the electromagnetic radiation into light in visible spectrum to affect activity of the neural cell 10. The body 102 of the device 100 is configured to allow electromagnetic radiation in infrared or near-infrared spectrum from a remote radiation system (not shown) to reach the light transducing materials 102 therein to perform upconversion. As shown, the device 100 in one embodiment is produced by sealing dry UCNPs in the body 102. The body 102 in this embodiment is formed by glass micro-pipette. By sealing the UCNPs, they do not directly contact the neurons. This effectively provides the UCNP-optogenetic devices of the present embodiment with the same biocompatibility as an optical fiber widely used in traditional optogenetic experiments. The device 100 in this embodiment is only ~100 μm in maximum diameter and less than 1 mg in weight. This dimension and weight which is greatly beneficial in preserving tissue integrity, as it leads to negligible brain lesion during surgical implantation.

Figure 1D:
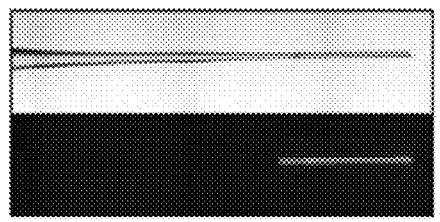

For remote delivery of NIR to the targeted body part of a behaving rodent in FIG. 1D, the invention provide a radiation system 200 in the form of a robotic laser projection system, which is capable of automatically tracing the animal's head and transmitting radiation to the animal's head. The radiation system 200 of one embodiment of the invention can place a single NIR illumination spot (3 cm in diameter) on the head of the rodent in real-time to achieve real time consistent NIR stimulation.

Figure 1E:
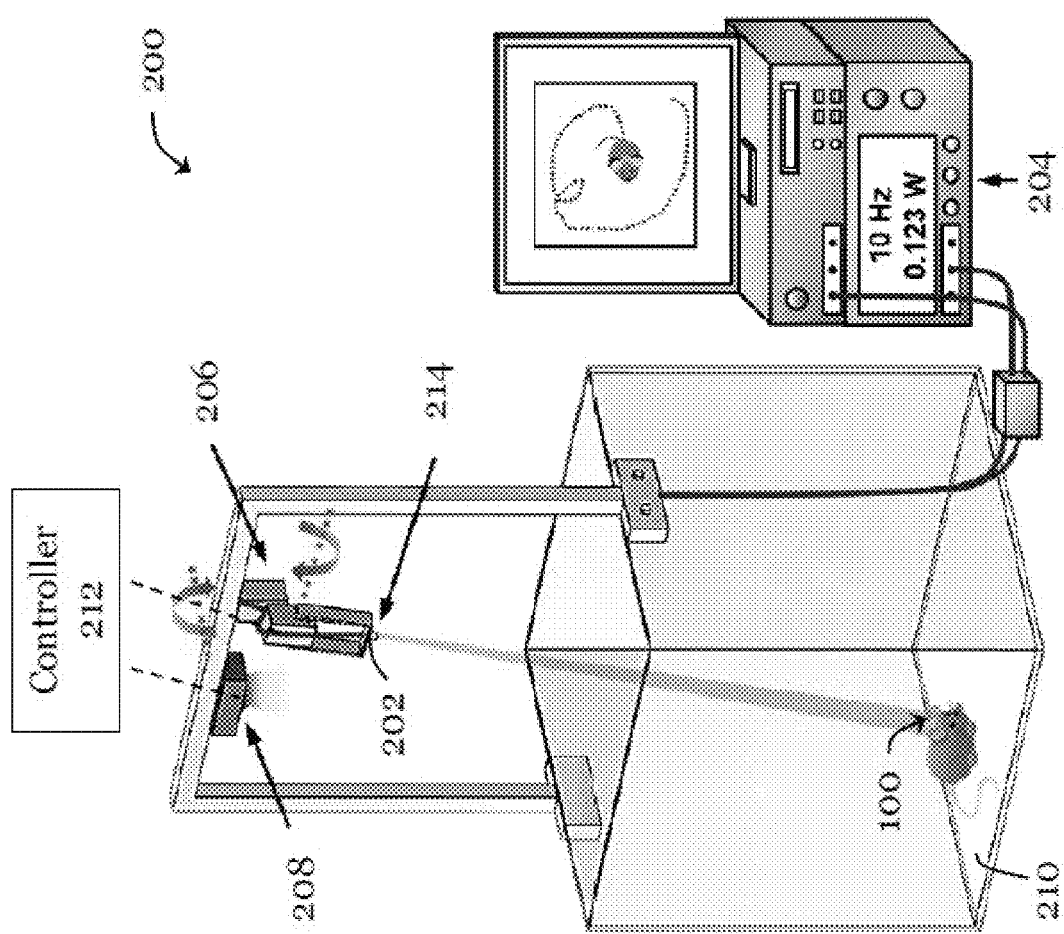

The radiation system 200 in FIG. 1E includes a radiation probe 202 arranged to be connected with a radiation source 204, for irradiating a wireless optogenetic device with electromagnetic radiation in infrared or near-infrared spectrum. A movement mechanism 206 is operably connected with the radiation probe 204 for moving the radiation probe 204. The system also includes a detector 208, such as a camera, for detecting a location of the wireless optogenetic device 100 cooperates and the controller 212 for controlling the movement mechanism to affect movement of the radiation probe 202 based on the detected location of the wireless optogenetic device 100. The controller 212 may be any of a processor, microprocessor, computer, information handling devices, etc. In operation, the system 200 cooperates such that the radiation probe 202 is arranged to irradiate the wireless optogenetic device 100 at the detected location with the electromagnetic radiation. Preferably, the movement mechanism 206 comprises a motorised arm to which the radiation probe is mounted. The movement mechanism 206 may be arranged to rotate or translate the radiation probe. In a preferred embodiment, the system 200 also includes a bounded platform 210 defining an area in which the subject can move. Optionally, one or more optical components (not shown) may be arranged in the system 200 to alter one or more properties of the electromagnetic radiation provided by the radiation source, the one or more properties comprises: the wavelength of the electromagnetic radiation, the intensity of the electromagnetic radiation, the power of the electromagnetic radiation, the duration of a pulse of the electromagnetic radiation, the power of a pulse of the electromagnetic radiation, and the frequency of pulses of the electromagnetic radiation. In one example, the source 204 may comprises a continuous wave laser diode. A collimator 214 for directing electromagnetic radiation emitted by the continuous wave laser diode may be provided at the outlet of the probe 202.

In the system 200 of FIG. 1E, the movement mechanism 206 includes a robotic arm formed by two rotational motors and a 3D-printed holding adaptor. The arm is placed ~50 cm above the bounded platform 210 and was used to project NIR illumination at arbitrary coordinates in a 40×40 cm experimental field. The control of the robotic arm and subsequently the placement of illumination spot were achieved using an image recognition program operated by the controller 212 and the detector 208. The implantable UCNP-ontogenetic device 100 and the autonomous radiation projection system 200 thus form an all-optical solution for tetherless control of brain function in freely moving animals.

Characterization of the Upconversion-Based Transducer Device

Engineered core-shell nanoparticles as shown in FIG. 2A can be used to make the UCNP transducer device. The nanostructure produces unique optical properties. UCNPs composed of lanthanide-doped NaYF4 were fabricated via a layer-by-layer growth process and used as light transducers in this example. The nano-synthesis protocol used in the invention offered exquisite control over particle size, morphology, and doping strategy with high reproducibility. The uniform spherical shape of the core, which has an average size of ~20 nm, is shown in the transmission electron microscopy images in FIG. 2B. The particle size is slightly increased with some morphological variation in the corresponding core-shell UCNPs used in this example, as shown in FIG. 2C. Upon NIR (980 nm) illumination, the UCNPs comprising $Tm^{3+}$ (or $Er^{3+}$) dopants in the core emitted blue (or green) light peaking at 470 nm (or 540 nm). After being packaged in a micro-ontogenetic device, the device typically produced an upconversion efficiency of ~4%, and the emission power of blue or green light was positively correlated with the input NIR power, as shown in FIGS. 2D and 2E. Though this efficiency is relatively low, the intensity of visible light emission could be sufficient for regular ontogenetic simulation, which has a power density requirement of 1-5 $mW/mm^2$.

Sufficient Tissue Penetration Under Safe NIR Irradiation

As NIR energy is not strongly absorbed by water or bio-molecules, NIR may in some applications penetrate deeper into tissue than visible light, and so is potentially highly phototoxic and may cause serious damage to human and animal eyes. NIR lasers are much less hazardous and safer to operate, as the major potential damage by NIR irradiation consists of the induced thermal effect. The thermal effects of NIR at an illumination power (8 $mW/mm^2$) much higher than the typical experimental settings required to drive UCNP-optogenetic devices were evaluated. Infrared imaging was used to monitor the temperature change of the sample in real time. As shown in FIGS. 3A and 3C, pulsed illumination of the 980 nm laser induced almost no temperature change on the skin of the animal. Furthermore, using an isolated rat brain, it was shown that the upconversion emission does not lead to any heating effects at the tip of the micro-optogenetic device, even though UNCPs were packaged there in a highly concentrated format, as shown in FIGS. 3B, 3D, and 3E. It should be noted that the UCNP-optogenetic device could still be activated to produce upconverted emission using safe NIR illumination, even after being inserted through a whole rat brain (~1 cm thick, FIG. 3C). This penetration depth is sufficient to accommodate all experiments involving neural stimulation in various brain structures. In the following experiments, the power settings for NIR irradiation were well below the conservative limits established for human skin exposure to 980 nm light (7.26 $mW/mm^2$).

Remote Regulation of Electrophysiological Activity in Rat Brains

To demonstrate effective neuronal stimulation by the NIR-actuated upconversion process, the UCNP-optogenetic device in one embodiment was implanted in the brain of a living animal to stimulate ChR2- or C1V1-expressing neurons, which were characterized by in vivo electrophysiology recordings, as shown in FIG. 4A. Micro-optogenetic devices containing $Tm^{3+}$ or $Er^{3+}$-doped UCNPs were implanted into the virus injection site along with tungsten electrodes (1.2 MΩ impedance). When the 980 nm laser (40 ms, 0.2 Hz, 7 $mW/mm^2$ for ChR2, or 40 ms, 0.2 Hz, 4.4 $mW/mm^2$ for C1V1) was applied, visible light from the UCNP-optogenetic device reliably induced neuronal spiking activity at the corresponding time points. Similar activation was not observed in virus-infected animals implanted with a null-optogenetic device (empty device without UCNPs), as shown in FIG. 4B. The temporal correlation between NIR illumination and evoked neuronal spiking was further confirmed using pen-stimulus time histograms (PSTHs) from representative electrode, as illustrated in FIGS. 4C-4D. These results proved the basic feasibility of upconversion-based NIR-optogenetics for controlling neural activity in brains of live animals without the need for in-tissue light delivery by tethered fiber optics.

Tetherless Transcranial Brain Stimulation in Behaving Mice

Figure 5A:
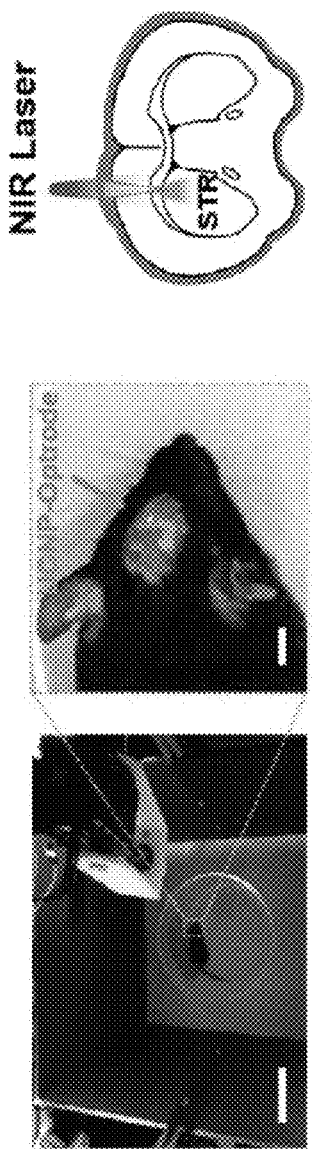
FIGS. 5A-5F illustrate tetherless, all-optical brain stimulation in behaving animals in one embodiment of the invention, and in particular.
Figure 5B:
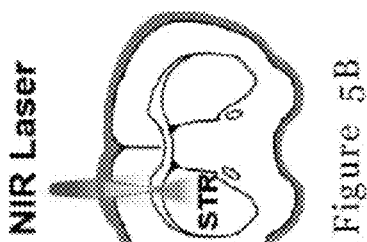
Figure 5C:
Figure 5D:
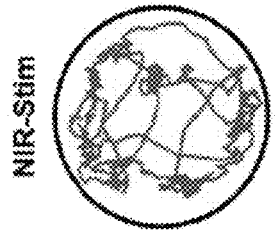
Figure 5E:
Figure 5F:
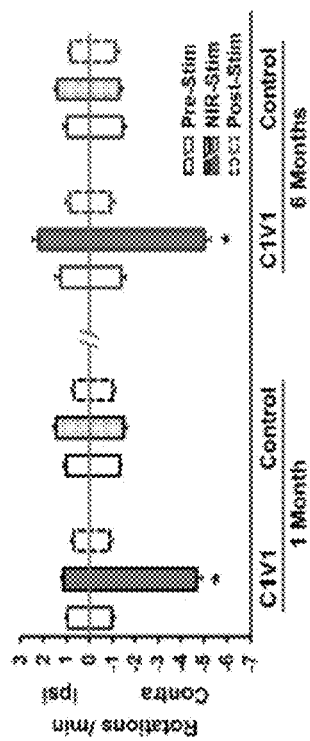

In combination with the robotic laser projection device in one embodiment as described, an all-optical tetherless system was implemented to test the effectiveness of the upconversion based neural stimulation strategy, to see if it can be used for behavioral conditioning in freely moving mice, as shown in FIG. 5A. In the demonstration, a micro-optogenetic device containing $Er^{3+}$-doped UCNPs was implanted in the cortical striatum (stereotactic coordinates: 1.1 mm posterior, 1.7 mm lateral, 3 mm ventral) of C1V1-infected mice for unilateral stimulation upon NIR illumination, as illustrated in FIG. 5B. The surgery site was fully covered by dental cement, which was further screwed to the surrounding skull to ensure long-term stability of the implants. The animals were individually placed in open experimental fields defined by a cylinder 30 cm in diameter and NIR illumination (10 ms pulse width, 20 Hz, 5 $mW/mm^2$) was consistently applied to their heads. The animals' movements were simultaneously monitored by video-tracking. FIGS. 5C-5E show that NIR could dramatically change the locomotion patterns of C1V1 mice following unilateral stimulation of the cortical striatum. Significantly more contraversive turning was induced in these animals than in control groups (4.68±0.26/min. vs. 1.48±0.17/min., mean±s.e.m., FIG. 5F). Furthermore, the UCNP-device was functional even after 6 months in the mouse brain (FIG. 5F), suggesting the utility of this technique in long-term chronic experiments. The above demonstrate that integration of upconversion technology and robotic instrumentation can provide an all-optical solution for flexible tetherless control of brain activity.

Deep Brain Stimulation

Figure 6A:
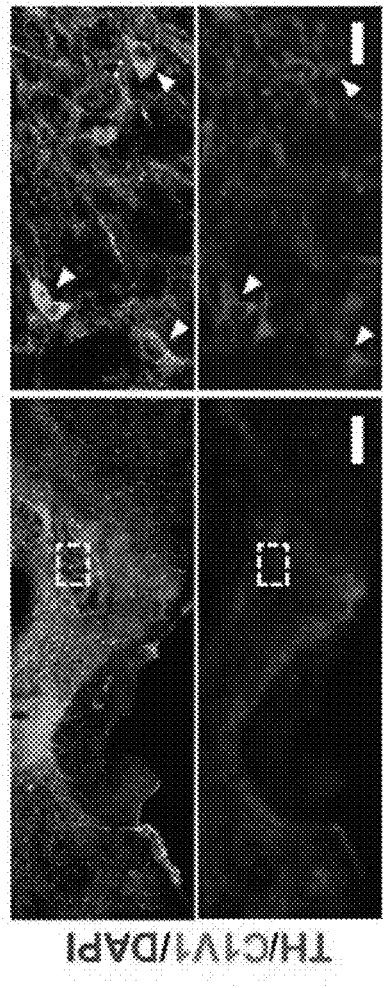
FIGS. 6A-6H illustrate NIR-conditioned location preference following deep brain stimulation in one embodiment of the invention, and in particular.
Figure 6B:
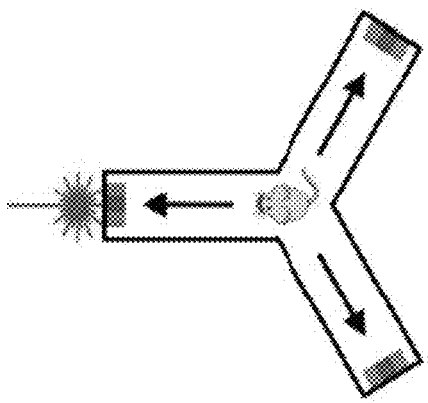
Figure 6C:
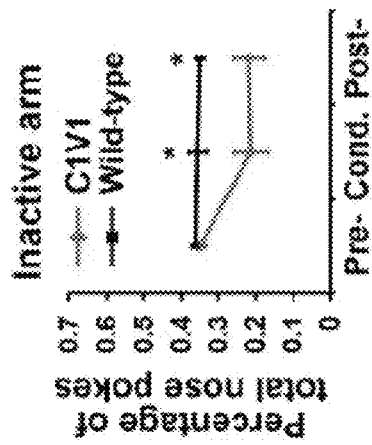
Figure 6D:
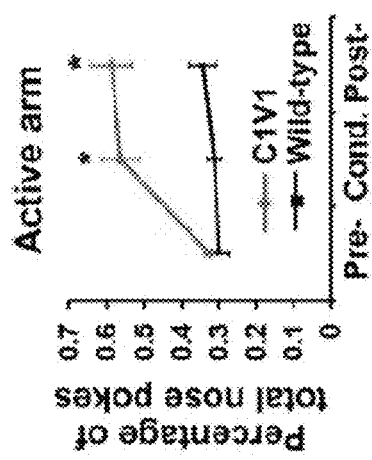
Figure 6E:
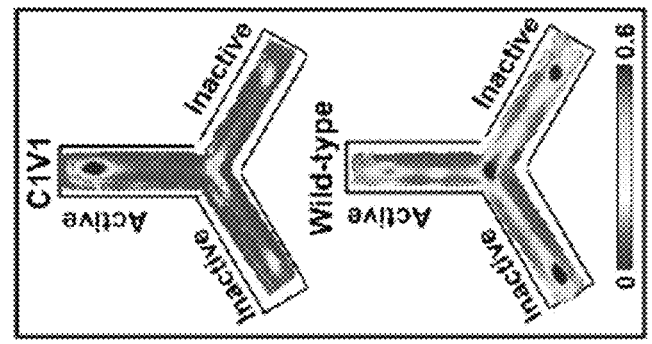
Figure 6F:
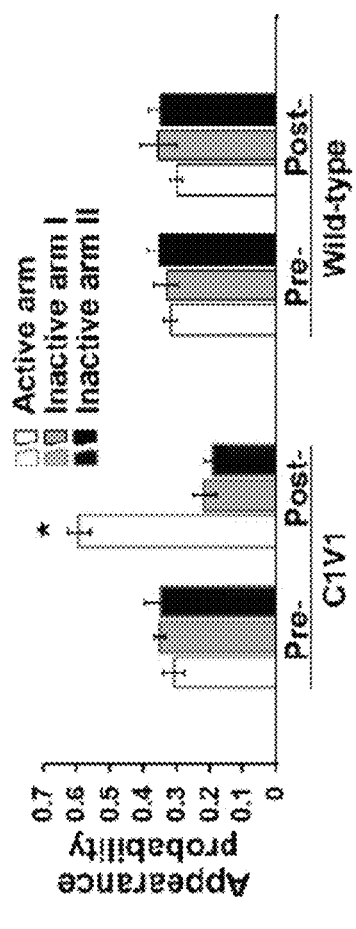
Figure 6G:
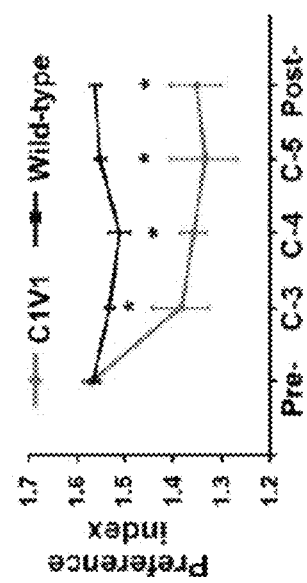
Figure 6H:
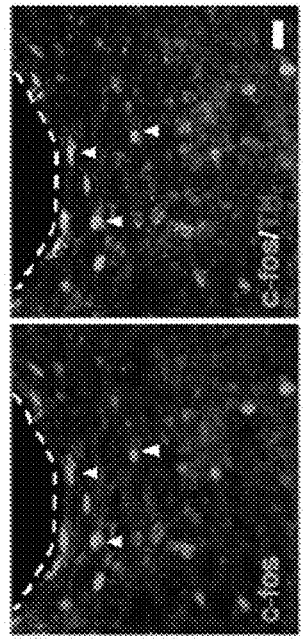

To show the application of the method and system in one embodiment of the invention for deep brain stimulation, the upconversion-based tetherless neural modulation method was further tested to stimulate the VTA (~4.5 mm deep) in mice. The device was used to control dopamine reward behavior in these animals while they explored a complex environment in a Y-shaped maze as shown in FIG. 6A. Phasic firing of dopaminergic neurons in the VTA is sufficient for behavioral conditioning. VTA tissue was transduced to express C1V1. Examination on whether NIR illumination could engage the animals in a location-oriented self-stimulation dopamine reward pathway was performed. As shown in FIG. 6B, many dopamine neurons (positive for tyrosine hydroxylase, $TH^+$) co-expressed C1V1 in the VTA region. Though it is possible that neurons in adjacent regions might also be infected to express ChR proteins due to the non-specific nature of the CaMKII promoter, proper stimulation of the VTA was further ensured by the precise placement of the microscale UCNP-optogenetic device using a stereotactic apparatus. In this experiment, mice were allowed to explore a Y-maze with three arms, each of which was equipped with a custom-made nose-poking apparatus at the distal end. Nose-poking at one specific arm ("Active")

was paired with 980 nm illumination (10 pulses, 20 Hz, 10 ms width, 5 mW/mm$^2$). As shown in FIGS. 6C-6G, C1V1 mice learned to self-stimulate their dopamine neurons by selectively approaching and poking in the "Active" arm, which triggered NIR illumination and effectively activated their VTA regions. After a five-day conditioning period, around 60% of the total nose pokes were made in the "Active" arm (FIG. 6C). This was accompanied by a significant drop in nose-pokes in the "inactive" arms (FIG. 6D). Accordingly, the mice also developed robust location preference to the "Active" arm, wherein they showed significantly higher appearance probability (59±3.5%, mean±s.e.m., n=5) than in the other two "inactive" arms, even in the post-conditioning period, which was devoid of further NIR illumination (FIGS. 6E and 6F). Animals receiving proper stimulation of the VTA had much more predictable movements after the NIR conditioning period, as indicated by a significant drop in the preference index (defined by information entropy of mouse appearance probabilities in all three arms, FIG. 6G). It was also observed that repeated NIR irradiation for one hour (5 mW/mm$^2$, 20 Hz, 10 ms width, 10 pulses were applied at the beginning of every minute) could induce strong expression of c-fos, which is a typical biochemical marker for neuronal activation, in C1V1$^+$/TH$^+$ dopamine neurons surrounding the UCNP-optogenetic device (FIG. 6H). About 76±2.3% (mean±s.e.m., n=5) of C1V1+ cells within 200 μm of the optogenetic device were activated by UCNPs to express c-fos. In these chronic experiments, which lasted for more than one month, the fully implantable device was well tolerated by the host brain. Only a small amount of glial activation surrounding the optogenetic device was observed due to minor surgical lesions, and there was no significant increases in the inflammatory response, as indicated by immunostaining of activated microglia. These results further established the utility and versatility of the tetherless system of the invention for controlling neural activity in deep brain regions; and highlighted its compatibility with vulnerable mouse models.

Implantation of Multiple UCNP-Optogenetic Devices

Figure 7B:
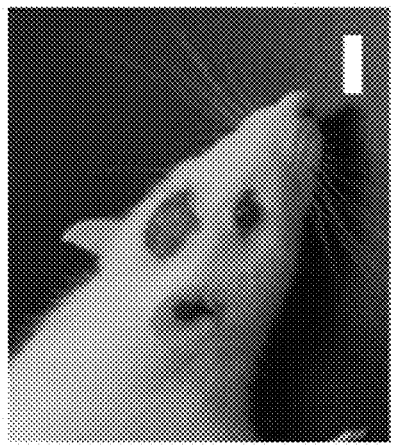
Figure 7A:
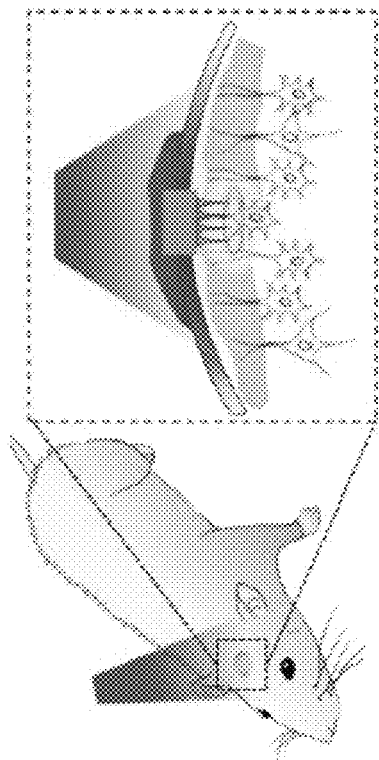
Figure 7C:
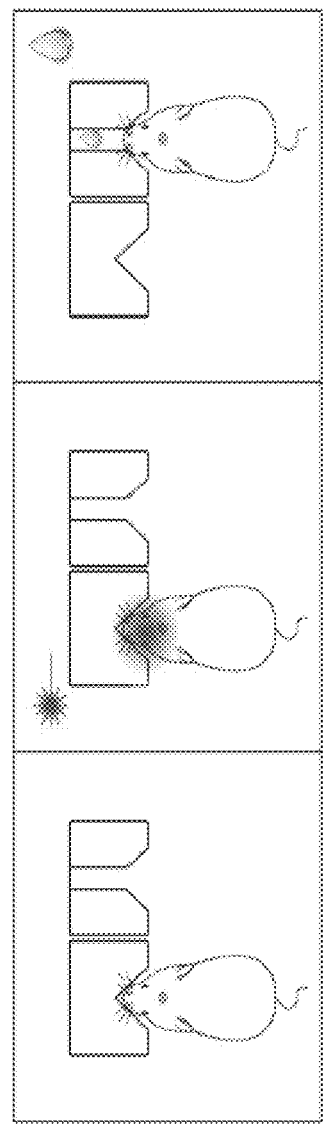
Figure 7D:
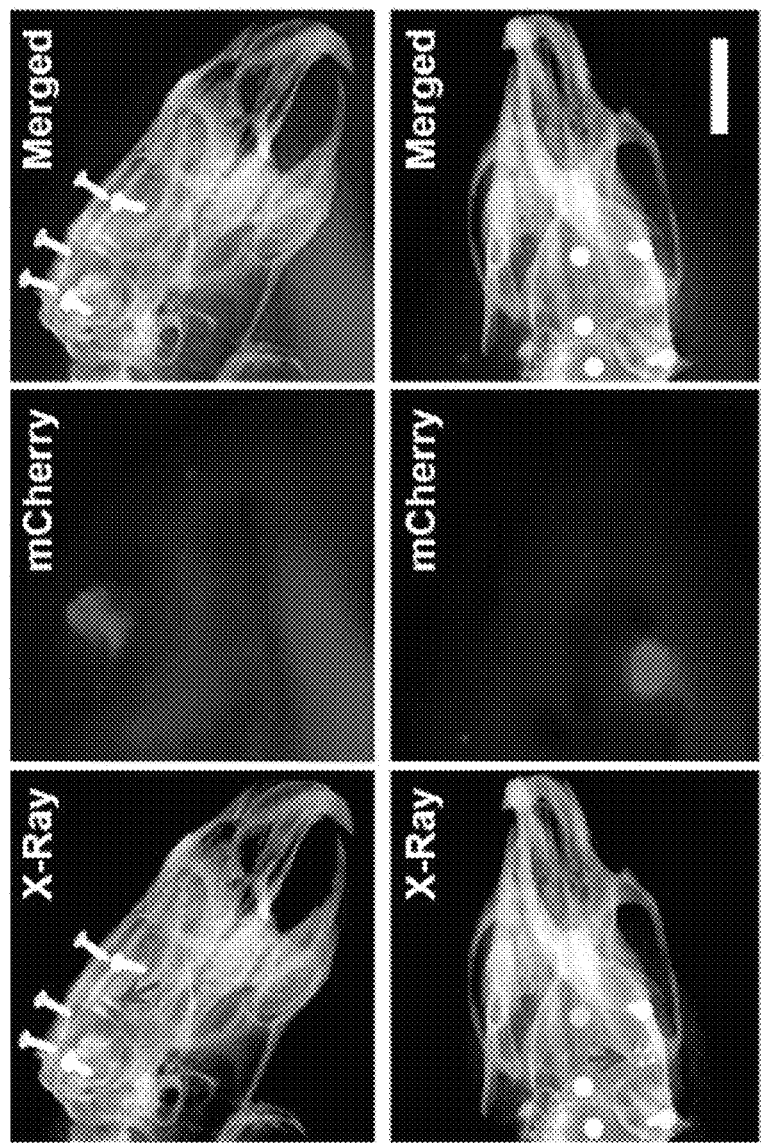

One of the advantages of the all-optical upconversion-based technique is the micro-scale size (~100 μm in diameter) and extremely light weight (less than 1 mg) of the implantable device. These characteristics enable multiple UCNP-optogenetic devices to be simultaneously implanted to achieve complex manipulation of brain function, as shown in FIGS. 7A-7C. As demonstrated here, an array of four UCNP-devices were implanted into the visual cortex of ChR2 rats to ensure sufficient activation. The device was used to pair water-seeking activity in a two-port operant chamber with neural stimulation in cortical tissue, which was controlled by a brief NIR exposure, as illustrated in FIG. 7C. The co-localization of the implanted UCNP-optogenetic devices and the ChR2-expressing region was directly validated using a multimodal animal imaging system with X-Ray and fluorescent capabilities (FIG. 7D). When an animal was placed in the dual-port chamber, it was required to insert its nose into the left port to initiate a trial after a variable holding period (800 to 1500 ms). A stimulus consisting of 10 NIR pulses (980 nm, 10 Hz, 50 ms pulse width, 1.5 mW/mm$^2$) was remotely applied over the animal's head. The activation of the visual cortex subsequently cued the animal to obtain a water reward from the right port (FIG. 7C). Successfully stimulated rats gradually responded to NIR signals after being trained for 3 to 4 days. These rats were triggered to obtain water rewards in a well-controlled pattern immediately after every NIR illumination cycle. Their performance was evaluated by either reaction time or success rate in obtaining rewards from the right port. On the 4th training day, the reaction times following the onset of the 980 nm laser were significantly reduced in properly stimulated subjects (FIG. 7e, p<0.001, paired Kruskal-Wallis test, n=4, at least 200 trials for each subject) when compared to animals in different control groups. As an animal's performance may depend on their expectation about the occurrence moment of the NIR cue, switching of one of the NIR cue was intentionally randomized using a varying holding period (800 to 1500 ms) after a nose-poke in the left port to prevent rats from predicting the stimulus. The reaction times were mostly between ~100 to ~400 ms in the ChR2 animals, and were significantly different when compared to the results obtained from animals in control groups, which had much more even distributions of reaction times during the period between 0 and 1500 ms (FIG. 7F). Accordingly, a successfully triggered trial was defined as a rewarded movement within a temporal window of 100 to 600 ms from the onset of NIR. After 4 days of training, the success rates of the NIR-triggered tasks gradually increased from ~50% to almost ~80% in the UCNP-optogenetic device-implanted animals receiving 980 nm laser illumination (FIG. 7G). This rate was significantly higher than those of the animals in the control groups, whose success rates were around or below 40% (FIG. 7h, p<0.001, one-way analysis of variance). Especially for trials requiring a long holding period of 1500 ms, which were the most difficult for the animals due to their limited patience, the success rate in properly stimulated animals was 3-fold higher than it was in wild-type (intact) animals (57±4.1% vs. 14±1.6%, mean±s.e.m., n=4). Taken together, these results suggest successful modulation of reflexive learning behavior in rats, further exemplifying the power of the upconversion-based tetherless neural stimulation technique of the invention.

EXPERIMENT

UCNP Synthesis and Characterization

The nanoparticles were synthesized using a modified procedure involving the growth of NaYF4:Yb/Er core nanoparticles followed by epitaxial coating of NaYF4 shells. Specifically, in a typical procedure for the synthesis of NaYF4:Yb/Er (or Tm) nanoparticles, 2 ml aqueous solution of RE(Ac)3 (0.2 M, RE=Y, Yb, Er, or Tm) was added to a 50 ml flask containing 3 ml of oleic acid and 7 ml of 1-octadecene. The mixture was heated at 150° C. for 30 min. before cooling to 50° C. Shortly thereafter, a methanol solution (5 ml) containing NH4F (1.6 mmol) and NaOH (1 mmol) was added and the solution was stirred for 30 min. After the methanol was evaporated, the solution was heated to 300° C. under argon for 1.5 hours and then cooled to room temperature. The resulting nanoparticles were precipitated by addition of ethanol, collected by centrifugation, washed with methanol and ethanol several times, and finally redispersed in cyclohexane. To coat the NaYF4 protection shell, an aqueous solution of Y(Ac)3 (0.2 M, 2 ml) was mixed with oleic acid (3 ml) and 1-octadecene (7 ml) in a 50 ml flask and subsequently heated at 150° C. for 30 min. before cooling to 50° C. NaYF4:Yb/Er (or Tm) core nanoparticles in cyclohexane (4 ml) were added along with a methanol solution (5 ml) of NH4F (1.6 mmol) and NaOH (1 mmol). The resulting mixture was stirred at 50° C. for 30 min., after which time the solution was heated to 300° C. under argon for 1.5 hours and then cooled to room temperature. The resulting nanoparticles were precipitated by addition of ethanol, collected by centrifugation, washed with methanol and ethanol several times, and redispersed in cyclohexane.

Animals

Sprague-Dawley (SD) rats and C57BL mice were used in this study. Male SD rats (8-9 weeks, 200-300 grams in weight) were used for the electrophysiology recordings and reaction-time task experiments. C57BL mice (6-8 week, 20-25 g in weight) were used in experiments involving deep brain stimulation (cortical striatum and VTA). Animals were randomly assigned to different experimental groups before the surgical procedures. No animals were excluded from analysis and no blinding was performed.

Sample Size and Statistics

Sample sizes were chose to be large enough to avoid overlap of the error bars of subsequent data points and to achieve statistically significant evaluations of different experimental conditions, as reflected by p-values less than 0.01 using hypothesis test analysis. The reported "n" numbers indicate biological replicates. For experiments involving stimulation of cortical striatum (FIG. 5), 4-5 mice were used for each condition. For experiments involving deep brain stimulation of VTA (FIG. 6), five mice were used for each condition. For analysis of NIR-triggered behavioral conditioning in reaction-time tasks (FIG. 7), four rats were used for each condition. All data used for statistical analysis were checked for distribution normality. For normally distributed data, ANOVAs were used to assess statistical significance among the different experimental conditions. Non-parametric Kruskal-Wallis tests were used when the assumption of normality was not met.

Fabrication of UCNP-Based Micro-Optogenetic Devices

UCNP-containing micro-optogenetic devices in this example were made from borosilicate glass capillaries (1.5 mm outer diameter and 1.0 mm inner diameter). The capillaries were pulled on a micropipette puller (Sutter Instruments, P-2000) to create micro-pipettes with tip sizes around 80 µm, which were used as packaging materials for UCNPs. The nanoparticles dispersed in cyclohexane were front-loaded into the tips of the micro-pipettes using a microinjector with negative holding pressure (Xenoworks, Sutter Instrument), which enabled delicate control of loading volume with nanoliter precision. After solvent evaporation, tips of micro-pipettes (filled with dry UCNPs) were sealed using a brief high-temperature treatment. A 3-5-mm segment was then cut from each glass micropipette and the back end was sealed with epoxy to form a UCNP-optogenetic device.

Virus Delivery in Animals

The adeno-associated viral (AAV) vectors AAV-CaM-KIIa-C1V1(E122T/E162T) TSmCherry (serotype 5), AAV-CaMKIIa-hChR2(H134R)-mCherry (serotype 5), and AAV-Syn-ChrimsonR-tdTomato (serotype 2) were used. Animals (rats/mice) were anesthetized with sodium pentobarbital (50 mg/kg). Anesthesia was maintained throughout the surgical operations. Fifteen minutes before the induction of anesthesia, atropine sulfate (0.05 mg/kg) was administered to inhibit tracheal secretions. The animals were then mounted on a stereotactic device for further operation.

For rats, a midline incision was made in the scalp after the liberal application of local anesthetics (xylocaine, 2%). A craniotomy was performed at a location 4.5-6.5 mm posterior and 3.0-5.0 mm lateral to the bregma to access the visual cortex, and the dura mater was removed. Viruses were injected at two locations with the following coordinates: 5.0/6.0 mm posterior, 4.0 mm lateral, and 1.0 mm ventral to bregma. Injections were made using a cannula connected to a syringe pump at a rate of 0.1 µl/min. (total volume, 1 µl). After the injection, the cannula was withdrawn, and the injection sites were cleaned with sterile saline and topped with silicone sealant (Kwik-cast, World Precision Instruments). The skin was then sutured back in place, and the rats were left to recover. During the procedures, the body temperatures of the rats were maintained at 37-38° C. using a heating blanket. After 3 weeks, the rats were prepared for further experiments.

For mice, after making an incision on the scalp following application of local anesthetics (xylocaine, 2%), a hole (0.6 mm diameter) was made on the skull at the appropriate location using an electric dental drill to access brain tissue. To infect the VTA, 0.5 µl of AAV viruses were injected into the brain at the following coordinate: 3.44 mm posterior, 0.48 mm lateral, and 4.4 mm ventral to bregma. To infect the cortical striatum, 0.5 µl of AAV viruses were injected into the brain tissue at the following coordinate: 1.1 mm posterior, 1.7 mm lateral, and 3 mm ventral to bregma. Injections were made at a rate of 0.02 µl/min. (total volume, 0.5 µl) using a glass micro-pipette connected to a syringe pump. After withdrawing the injection micropipette, the injection sites were cleaned with sterile saline, and the skin was sutured. During the procedures, the body temperatures of the mice were maintained at 37-38° C. using a heating blanket. The mice were used for further experiments three weeks later.

UCNP-Optogenetic Device Implantation

Implantation of UCNP-based micro-optogenetic devices was performed 3 weeks after virus injection using a stereotactic apparatus. During the surgical operations, the animals were anesthetized as described above, and a similar craniotomy was performed. The silicone sealant was removed before implanting any devices.

For acute in vivo electrophysiology experiments, bundles combining a UCNP-optogenetic device and a tungsten electrode were inserted into the virus injection sites (5.0-6.0 mm posterior, 4.0 mm lateral, and 1.0 mm ventral to bregma). Electrical measurements were performed in anesthetized animals immediately afterwards. For behavioral experiment in rats, four UCNPoptogenetic devices were inserted into tissues around the injection sites (5.0-6.0 mm posterior, 3.5-4.5 mm lateral, and 1.0 mm ventral to bregma). For behavioral experiments in mice, a single UCNPoptogenetic device was inserted into the appropriate brain region at the virus injection site. For cortical striatum stimulation, the stereotactic coordinates were 1.1 mm posterior, 1.7 mm lateral, and 3 mm ventral to bregma. For VTA stimulation, the stereotactic coordinates were 3.44 mm posterior, 0.48 mm lateral, and 4.5 mm ventral to bregma. All animals were allowed to recover for at least one week before proceeding to behavioral experiments.

Behavioral Study in Rats Using Reaction-Time Tasks

Behavioral studies in freely moving animals were performed at least one week after all surgical operations. After the recovery period, animals with significant weight loss were excluded from the experiments. The subjects were trained in a two-port operant chamber to characterize their response to remote NIR stimulation. In this task, an animal, which was previously maintained using a restricted water supply, was first habituated in the chamber for familiarization with the nose-poke and water-seeking tasks for one day. It was then trained to poke into the left port (waiting hole) to initiate a trial and required to stand still for a random waiting period (800, 1000, 1200 or 1500 ms) before the application of sequences of 10 NIR pulses (980 nm, 50-ms pulse width, 1.5 mW/mm$^2$) from an overhead light source. This stimulation then cued the animals to obtain water rewards from the right port (rewarding hole). The reaction times and success rates were used as major parameters to access the subject's performance. Though the water reward was presented in the rewarding hole for 2 seconds after each NIR cue, only trials with reaction times longer than 100 ms and shorter than 600 ms were considered successful NIR-stimulated trials.

NIR-Conditioned Location-Preference in Mice

NIR stimulation of the VTA was performed in mice to condition their location preference. Briefly, C1V1-infected mice (with implanted UCNP-optogenetic devices) were prepared for experiments by mildly restricting their water supply to facilitate behavioral responses. Mice were then placed in an unbiased Y-maze with three compartments. Each arm of the Y-maze was 30 cm long and 5 cm wide, and was connected by a triangular region (total area of 460 cm2). Homemade nose-poke devices were installed at the distal ends of the arms and the numbers of nose-poke by the mice were automatically recorded using a commercial system (Tucker-Davis Technologies).

The mouse was first placed in the Y-maze and allowed to freely explore the entire apparatus for one day (pre-conditioning) in order to familiarize itself to the environment. From day 2 to day 3 (conditioning phase I), the animal was further allowed to explore the Y-maze. During this time, a nose-poke in the "Active" arm was paired with a 500-ms 980 nm illumination (10 ms pulse width, 20 Hz, 5 mW/mm$^2$), which was used to stimulate the VTA in the mouse brain. The conditioning was completed daily until 300 nose-pokes were achieved. From day 4 to day 6 (conditioning phase II), the mice were allowed to explore the Y-maze for one hour each day, and their behaviors were recorded by a camera. Nose-pokes were still paired with NIR illumination in the "Active" arm. After the conditioning period, the animals were allowed to rest for one day. From day 8 to day 9 (post-conditioning), NIR illumination was removed from the system and the mouse was placed in the Y-maze for one hour each day. The behaviors of the mice were recorded on camera for later analysis.

To analyze the animal's behavior in the Y-maze, the recorded one-hour-long video was first sampled at 1 Hz to produce a stack of time-course images. The whole stack was then averaged at every pixel to derive a background reference, which was subtracted from the raw images to extract the "mouse signal". The location of the mouse at a specific time point was determined using the "mouse signal". Summing up all "mouse signals" from all images resulted in a map of mouse activity, wherein areas of higher appearance frequency were colored in red, and those of lower frequency were colored in yellow. A template of the Y-maze was used to filter out noise signals outside of the mouse movement areas. Information entropy of mouse appearance probability in each of the three arms was used as an indicator of the predictability of mouse movement (preference index), which reflects the animal's location preference following conditioning by NIR stimulation of the VTA deep in the mouse brain. The information entropy H(X) was calculated as:

$$H(X) = -\sum_{i=1}^{3} P(x_i) \log_2 P(x_i)$$

given that $X \in \{x_1, x_2, x_3\}$ and $P(x_i)$ were the probability of mouse appearance within $\text{Arm}_i$ of the Y-maze.

Robotic Laser Projection System and Stimulation of Cortical Striatum

To accommodate flexible and consistent brain stimulation using the upconversion-based technique, a robotic laser projection system was developed for automatic tracing of the mouse head. This system was used to place a single NIR illumination spot on the mouse's head in real-time. In this system, two rotational motors (AX-18A, Dynamixel) and a 3D-printed holding beam were assembled to form a robotic arm, which was placed ~50 cm above the animal. This arm was used to project NIR illumination at arbitrary coordinates in a 40×40 cm experimental field. A high-speed camera was installed beside the robotic arm for video recording. Before the experiments, the coordinates of the experimental field (40×40 cm) were digitized and mapped with a resolution of 0.25 mm (0.29°) using a calibration scan. Movement of the robotic arm was achieved using a custom-developed program in Python, which was used for the automatic identification of the targeting spot on the animal's head. The image processing procedure in this example comprises the following 6 steps: 1) every frame from the video recording was processed in real-time; 2) a region of interest was defined; 3) the color space was transformed from RGB to HSV; 4) a binary mask was generated using the HSV image; 5) blob detection was used identify large features on the animal's head; 6) after removing the noise blobs, the average coordinates of the largest three blobs were taken as the target position and then sent to the control board for laser projection.

For stimulation of the mouse cortical striatum, a cylinder 30 cm in diameter was placed in the laser projection system for better visualization. Mice were placed in the cylinder and allowed to behave freely. A testing cycle consisted of three one-minute sessions: pre-stimulation, stimulation, and post-stimulation. NIR illumination was applied only during the stimulation session using the robotic projection system (10 ms pulse width, 20 Hz, 5 mW/mm$^2$). The animal's movements and turning behavior were then quantitatively analyzed based on the recorded movie.

Immunohistochemistry

To perform immunohistochemistry, rats/mice were anesthetized with pentobarbital and transcardially perfused with 0.9% NaCl and 4% paraformaldehyde. Brains were extracted and fixed for at least 1 day at 4° C. Samples were then bathed in 30% sucrose solution (diluted in phosphate-buffered saline [PBS]) until the brain tissue settled to the bottom. The brains were then cut into 50-μm-thick slices by frozen sectioning (Cryostar NX70, Thermo Scientific) and mounted on glass slides. All brain slices were thoroughly rinsed with PBS and blocked in 4% bovine serum albumin in Tris-buffered saline containing 0.25% Triton X-100 overnight at 4° C. The slices were then incubated with primary antibodies overnight at 4° C. and rinsed thoroughly with Tris-buffered saline before incubation with secondary antibodies for 1 hour at room temperature. The stained brain slices were then rinsed with PBS and mounted on glass slides for imaging. Samples were imaged using a confocal scanning laser microscope equipped with a 40× water immersion objective (TCS SP8, Leica Microsystems). The primary antibodies used in this study included rabbit anti-c-fos (Abcam, ab190289, 1:2,000 dilution), rabbit anti-GFAP (Millipore, AB5804, 1:1000 dilution) goat anti-Iba1 (Abcam, ab5076, 1:500), and sheep antityrosine hydroxylase (Abcam, ab113, 1:500).

Live Animal Imaging

In vivo imaging of live animals was carried out using a multi-model imaging system (In-Vivo Xtreme, Bruker). The rats/mice were anesthetized by injection of sodium pentobarbital (50 mg/kg). Both X-ray and fluorescence images were acquired. A 600 nm emission filter (35 nm band-pass window) was used for mCherry. In order to excite UCNP-optogenetic devices, a 980 nm laser system was custom-installed within the animal imager and illumination was applied from above. A 535 nm emission filter (35 nm band-pass window) was used for UCNPs emitting green light.

Advantages

The above embodiment provides an all-optical system for tetherless control of brain activity using upconversion-based implantable micro-devices. With optogenetics emerging as an important technical advance in neuroscience research, optical intervention has become increasingly popular for selective interrogation of circuit elements in normal and pathological conditions. A typical optogenetic experiment however usually requires the insertion of fiber optics that are tethered to external light sources. This may be a problem for chronic or longitudinal experiments in behaving animals and underscores the need for tether-free brain stimulation strategies. The system and method above embodiment of the invention combines upconversion technology with robotic instrumentation and provides an alloptical solution for flexible tetherless control of brain activity. In the experiments, UCNPs were packaged in glass micro-pipettes to make fully implantable devices, which were used as transducers to convert tissue-penetrating NIR light to higher-energy visible wavelengths matching the activation spectra of commonly used opsin proteins. Traditional optogenetic experiments can thus be performed using remotely applied NIR as the stimulus signal. In contrast to wireless optogenetic strategies utilizing radio-frequency signals to power implanted LEDs/micro-LEDs, the upconversion-based method of the invention does not require any electronic components. Therefore, the fully implantable UCNP-device is extremely small (~100 μm in diameter) and light (less than 1 mg). This is critical in alleviating stress in small animals and helps to reduce surgical lesions resulting from implantation procedures.

Using the system and method of the above embodiment, efficient transcranial neural stimulation at various depths in mouse or rat brains (~4.5 mm at the VTA, ~3 mm at the cortical striatum, and ~1 mm at visual cortex) was demonstrated. It was shown that the stimulation depth can potentially be increased to beyond ~1 cm and span a whole rat brain. This kind of deep brain stimulation may be challenging when using alternative optical methods utilizing red-shifted rhodopsins, such as Chrimson, which is activated by 660 nm light. The superior penetration capability of the technique of the invention is achieved in a synergistic manner by combining the advantages of NIR lasers and transparent glass microoptogenetic devices, which help guide and facilitate the delivery of NIR into deep brain regions. In addition to their transducing functions, which bridge the spectral gap between NIR and VIS, the packaged UCNPs also result in concentrated emission from a tiny spot at the tip of the micro-optogenetic device (~100 μm in diameter) to provide visible light at sufficiently high power densities in close proximity to brain tissue for optogenetic stimulation. Without UCNPs, the same transparent optogenetic device was not able to conduct visible light for neural stimulation if the illumination was applied from outside the brain, suggesting the pivotal role of UCNPs in this novel technique.

Even though upconversion is generally a process with low efficiency, the emission from the UCNP-optogenetic devices (doped with $Tm^{3+}$ or $Er^{3+}$) was sufficient to effectively activate neurons expressing ChR2 or C1V1. As indicated by fluorescent imaging in live animals, the visible light emitted from UCNP-optogenetic devices could extend as far as two hundred microns. The optogenetic devices thus have a neural activation range of several cell layers, which is a similar distance to that achieved using optical fibers, as indicated by c-fos expression after neuronal activation. In addition, the highly tunable optical properties of UCNPs can potentially be tailored to match more ChR variants, further providing potential flexibility for experiments requiring complex activation or silencing patterns. The upconversion process results sequential discrete absorption of two or more lower-energy photons, therefore, NIR-optogenetic control can be achieved using inexpensive and readily available continuous-wave diode lasers. The technique of the invention is thus highly cost-effective and simple in its practical implementation. The upconversion-based tetherless neural stimulation system of the invention, along with the in-house developed robotic laser projection equipment, can be readily set up in laboratories. With further optimization of different components in the system, such as the packaging of UCNPs, implantation procedures, and laser illumination parameters, etc., the neural stimulation range, effectiveness, and complexity could potentially be further improved. The invention thus provides an innovative demonstration of an upconversion-based, all-optical, tetherless brain stimulation strategy in behaving animals, which would benefit both basic and translational neuroscience research.

It will be appreciated that where the methods and systems of the invention are either wholly implemented by computing system or partly implemented by computing systems then any appropriate computing system architecture may be utilized. This will include stand-alone computers, network computers and dedicated hardware devices. Where the terms "computing system" and "computing device" are used, these terms are intended to cover any appropriate arrangement of computer hardware capable of implementing the function described.

It will be appreciated by persons skilled in the art that further variations and/or modifications may be made to the invention as shown in the specific embodiments. For example, the wireless optogenetic device can be of different shape, other than being tapered. The wireless optogenetic device can be a cross section of any other shape. The weight and dimension of the device may vary depending on the applications. The wireless optogenetic device can be made of other non-glass materials, such as plastic. The wireless optogenetic device need not be transparent to the human eye, so long as it allows the electromagnetic radiation to pass. The device can be coated with a light reflecting layer and with one or more optical windows for selectively emitting light. The light transducing materials used need not be UPSCs, but can be other materials operable to transduce light by upconversion and affect activity of the neural cell. The light transducing materials may be wet, not dry. In some cases, different types of UPSCs can be used. The size of the UPSCs may vary. The electromagnetic radiation used need not be in NIR spectrum but could be in IR spectrum. The radiation system can be of alternative setup. For example, the movement mechanism may move the probe by moving a frame connected with the probe. The radiation system may not include a bounded platform that defines a bounded area. The present embodiments are, therefore, to be considered in all respects as illustrative and not restrictive.

The invention claimed is:

1. A wireless optogenetic device arranged to be placed in proximity to a neural cell of a subject, comprising:
a body with a receptacle made of glass and with an optical inlet, the receptacle defining an interior space and an outer surface;
a light reflective layer coated on the outer surface of the receptacle, the light reflective layer including one or more optical windows; and
light transducing materials arranged inside the interior space of the receptacle,
wherein the light transducing materials, when exposed to an electromagnetic radiation in infrared or near-infrared spectrum, are arranged to up-convert the electromagnetic radiation into light in visible spectrum to affect activity of the neural cell;
wherein the optical inlet of the body is configured to allow the electromagnetic radiation in infrared or near-infrared spectrum from a remote radiation system to reach the light transducing materials to perform up-conversion such that the up-converted light is emitted from the one or more optical windows.

2. The wireless optogenetic device of claim 1, wherein the wireless optogenetic device is free of electrical components.

3. The wireless optogenetic device of claim 1, wherein the body is tapered towards a tip and the light transducing materials are at least arranged at the tip.

4. The wireless optogenetic device of claim 1, wherein the body is biocompatible.

5. The wireless optogenetic device of claim 1, wherein the body is substantially transparent.

6. The wireless optogenetic device of claim 1, wherein the body has a plurality of optical windows, and at least two different types of light transducing materials are arranged at two different optical windows of the plurality of optical windows.

7. The wireless optogenetic device of claim 1, wherein the body is sealed to enclose the light transducing materials.

8. The wireless optogenetic device of claim 1, wherein the light transducing materials comprises nanomaterials.

9. The wireless optogenetic device of claim 8, wherein the nanomaterials comprise lanthanide-doped nanoparticles.

10. The wireless optogenetic device of claim 8, wherein the nanomaterials comprise $NaYF_4$-based nanoparticles.

11. The wireless optogenetic device of claim 1, wherein the electromagnetic radiation has a wavelength of 700 nm to 1100 nm.

12. The wireless optogenetic device of claim 1, wherein the neural cell comprises neurons expressing opsin proteins.

13. The wireless optogenetic device of claim 1, wherein the neural cell is a neural cell in a central nervous system or a peripheral nervous system of the subject.

14. A radiation system arranged to remotely irradiate a wireless optogenetic device placed in proximity to a neural cell of a subject; the wireless optogenetic device comprising a body with a receptacle made of glass and with an optical inlet, the receptacle defining an interior space and an outer surface; a light reflective layer coated on the outer surface of the receptacle, the light reflective layer including one or more optical windows, and light transducing materials arranged inside the interior space of the receptacle; wherein the light transducing materials, when exposed to an electromagnetic radiation in infrared or near-infrared spectrum, are arranged to up-convert the electromagnetic radiation into light in visible spectrum to affect activity of the neural cell; and wherein the optical inlet of the body is configured to allow electromagnetic radiation in infrared or near-infrared spectrum from a remote radiation system to reach the light transducing materials to perform up-conversion such that the up-converted light is emitted from the one or more optical windows;
the radiation system comprising:
a radiation probe arranged to be connected with a radiation source, for irradiating a wireless optogenetic device with electromagnetic radiation in infrared or near-infrared spectrum;
a movement mechanism operably connected with the radiation probe for moving the radiation probe;
a detector for detecting a location of the wireless optogenetic device; and
a controller for controlling the movement mechanism to affect movement of the radiation probe based on the detected location of the wireless optogenetic device such that the radiation probe is arranged to irradiate the wireless optogenetic device at the detected location with the electromagnetic radiation.

15. The radiation system of claim 14, further comprising the radiation source.

16. The radiation system of claim 14, wherein the radiation probe is arranged to provide electromagnetic radiation with a wavelength of 700 nm to 1100 nm.

17. The radiation system of claim 14, further comprising a bounded platform defining an area in which the subject can move.

18. The radiation system of claim 14, wherein the movement mechanism is arranged to rotate or translate the radiation probe.

19. The radiation system of claim 18, wherein the movement mechanism comprises a motorised arm to which the radiation probe is mounted.

20. The radiation system of claim 14, wherein the radiation source comprises continuous wave laser diode.

21. The radiation system of claim 20, wherein the radiation probe comprises a collimator for directing electromagnetic radiation emitted by the continuous wave laser diode.

22. The radiation system of claim 14, wherein the detector is arranged for tracking real time movement of the subject; and wherein the controller is arranged to control the movement mechanism to affect movement of the radiation probe to continuously irradiate the wireless optogenetic device with the electromagnetic radiation during movement of the subject.

23. The radiation system of claim 14, further comprising an optical component arranged to alter one or more properties of the electromagnetic radiation provided by the radiation source, the one or more properties comprises: the wavelength of the electromagnetic radiation, the intensity of the electromagnetic radiation, the power of the electromagnetic radiation, the duration of a pulse of the electromagnetic radiation, the power of a pulse of the electromagnetic radiation, and the frequency of pulses of the electromagnetic radiation.

24. The radiation system of claim 14, wherein the detector comprises a camera.

25. A system for controlling activity of a neural cell of a subject, comprising:
a wireless optogenetic device arranged to be placed in proximity to a neural cell of a subject, comprising a body with a receptacle made of glass and with an optical inlet, the receptacle defining an interior space and an outer surface, a light reflective layer coated on the outer surface of the receptacle, the light reflective layer including one or more optical windows, and light transducing materials arranged inside the interior space of the receptacle, wherein the light transducing materials, when exposed to an electromagnetic radiation in infrared or near-infrared spectrum, up-convert the electromagnetic radiation into light in visible spectrum to affect activity of the neural cell; and allow electromagnetic radiation in infrared or near-infrared spectrum from a remote radiation system to reach the light transducing materials via the optical inlet of the body to perform up-conversion such that the up-converted light is emitted from the one or more optical windows;

a radiation system arranged to remotely irradiate the wireless optogenetic device, comprising:

a radiation probe arranged to be connected with a radiation source, for irradiating a wireless optogenetic device with electromagnetic radiation in infrared or near-infrared spectrum;

a movement mechanism operably connected with the radiation probe for moving the radiation probe;

a detector for detecting a location of the wireless optogenetic device; and a controller for controlling the movement mechanism to affect movement of the radiation probe based on the detected location of the wireless optogenetic device such that the radiation probe is arranged to irradiate the wireless optogenetic device at the detected location with the electromagnetic radiation.

26. A method for controlling activity of a neural cell of a subject, comprising:

placing a wireless optogenetic device in proximity to the neural cell of the subject, the wireless optogenetic device comprising a body with a receptacle made of glass and with an optical inlet, the receptacle defining an interior space and an outer surface;

a light reflective layer coated on the outer surface of the receptacle, the light reflective layer including one or more optical windows; and light transducing materials arranged inside the interior space of the receptacle;

wherein the light transducing materials, when exposed to electromagnetic radiation in infrared or near-infrared spectrum, are arranged to up-convert the electromagnetic radiation into light in visible spectrum to affect activity of the neural cell; and wherein the optical inlet of the body is configured to allow the electromagnetic radiation in infrared or near-infrared spectrum from a remote radiation system to reach the light transducing materials to perform up-conversion such that the up-converted light is emitted from the one or more optical windows; and remotely irradiating the wireless optogenetic device using the remote radiation system such that the irradiation enters the wireless optogenetic device via the optical inlet.

27. The method of claim 26, further comprising:

detecting, using the remote radiation system, a location of the wireless optogenetic device; and irradiating, using the remote radiation system, the wireless optogenetic device based on the detected location.

28. The method of claim 27, wherein the step of detecting a location of the wireless optogenetic device comprises:

tracking real time movement of the subject; and wherein the step of irradiating the wireless optogenetic device based on the detected location comprises:

continuously irradiating the wireless optogenetic device with the electromagnetic radiation during movement of the subject.

29. The method of claim 26, wherein the placing and irradiating steps are performed in vivo for in vivo behavioral conditioning or behavioral control of the subject.

30. A method of manufacturing a wireless optogenetic device, comprising:

(a) forming a body with a receptacle made of glass and with an optical inlet with open ends, the receptacle defining an interior space and an outer surface; and a light reflective layer coated on the outside surface of the receptacle, the light reflective layer including one or more optical windows, and light transducing materials arranged inside the interior space of the receptacle, wherein the light transducing materials, when exposed to an electromagnetic radiation in infrared or near-infrared spectrum, up-convert the electromagnetic radiation into light in visible spectrum to affect activity of the neural cell; and allow electromagnetic radiation in infrared or near-infrared spectrum from a remote radiation system to reach the light transducing materials to perform up-conversion such that the up-converted light is emitted from the one or more optical windows;

(b) placing the light transducing materials in the receptacle; and (c) sealing at least one end of the receptacle to form the wireless optogenetic device.

31. The method of claim 30, wherein the receptacle is substantially transparent.

32. The wireless optogenetic device of claim 1, wherein the body is made by a glass micro-pipette.

33. The wireless optogenetic device of claim 1, wherein the body is made of borosilicate glass.

* * * * *